US012430202B2

(12) United States Patent
Oboukhov et al.

(10) Patent No.: US 12,430,202 B2
(45) Date of Patent: Sep. 30, 2025

(54) NESTED ERROR CORRECTION CODES FOR DNA DATA STORAGE

(71) Applicant: Western Digital Technologies, Inc., San Jose, CA (US)

(72) Inventors: Iouri Oboukhov, Rochester, MN (US); Richard Galbraith, Rochester, MN (US); Niranjay Ravindran, Rochester, MN (US); Jonas Goode, Lake Forest, CA (US); Weldon M. Hanson, Rochester, MN (US)

(73) Assignee: Western Digital Technologies, Inc., San Jose, CA (US)

( * ) Notice: Subject to any disclaimer, the term of this patent is extended or adjusted under 35 U.S.C. 154(b) by 79 days.

(21) Appl. No.: 18/499,370

(22) Filed: Nov. 1, 2023

(65) Prior Publication Data
US 2024/0185959 A1 Jun. 6, 2024

Related U.S. Application Data

(60) Provisional application No. 63/386,068, filed on Dec. 5, 2022.

(51) Int. Cl.
*H03M 13/00* (2006.01)
*G06F 11/10* (2006.01)
(Continued)

(52) U.S. Cl.
CPC .......... *G06F 11/1004* (2013.01); *G06F 16/27* (2019.01); *G16B 50/50* (2019.02);
(Continued)

(58) Field of Classification Search
CPC .......... G06F 11/1004; H03M 13/1105; H03M 13/1148; G11C 13/02
See application file for complete search history.

(56) References Cited

U.S. PATENT DOCUMENTS

| 8,407,554 B2 | 3/2013 | Kermani |
| 8,937,564 B2 | 1/2015 | Aloni |

(Continued)

FOREIGN PATENT DOCUMENTS

| CN | 118138060 A | 6/2024 |
| EP | 3416076 A1 | 12/2018 |

(Continued)

OTHER PUBLICATIONS

Nakata et al., "Synchronization and Asymmetric Error Correction for Nanopore Sequencing," 2021 IEEE International Conference on Consumer Electronics—Taiwan, pp. 1-2, (2021).

(Continued)

*Primary Examiner* — Esaw T Abraham
(74) *Attorney, Agent, or Firm* — Patent Law Works LLP

(57) ABSTRACT

Example systems and methods for using nested error correction codes for DNA data storage are described. A data unit may be encoded in a set of oligos. Using an error correction code, such as an LDPC code, a codeword may be determined for the data unit that is a multiple of the data payload capacity of each oligo. The codeword may be divided among the set of oligos, along with corresponding redundancy data. Any number of additional levels of nested error correction codes may be implemented by aggregating sets of smaller codewords into larger codewords and storing the corresponding redundancy data in the set of oligos. Each nested level may be aggregated from the set of oligos and decoded using the corresponding error correction code matrix and set of redundancy data as needed, such as in response to failure to decode codewords at a lower level.

20 Claims, 8 Drawing Sheets

(51) Int. Cl.
  *G06F 16/27* (2019.01)
  *G16B 50/50* (2019.01)
  *H03M 13/11* (2006.01)
  *G11C 13/02* (2006.01)

(52) U.S. Cl.
  CPC .... *H03M 13/1105* (2013.01); *H03M 13/1148* (2013.01); *G11C 13/02* (2013.01)

(56) References Cited

U.S. PATENT DOCUMENTS

| | | | |
|---|---|---|---|
| 9,234,239 | B2 | 1/2016 | Sikora |
| 9,830,553 | B2 | 11/2017 | Chen |
| 10,027,347 | B2 | 7/2018 | Le Scouarnec |
| 10,370,246 | B1 | 8/2019 | Milenkovic |
| 10,423,341 | B1* | 9/2019 | Kermani ............. G06F 3/0631 |
| 10,566,077 | B1 | 2/2020 | Milenkovic |
| 10,650,312 | B2 | 5/2020 | Roquet |
| 10,742,233 | B2 | 8/2020 | Erlich |
| 10,810,495 | B2* | 10/2020 | Roth ...................... H03M 7/40 |
| 10,818,378 | B2 | 10/2020 | Hutchison, III |
| 10,917,109 | B1* | 2/2021 | Dimopoulou ....... H03M 7/3088 |
| 10,956,806 | B2 | 3/2021 | Masuda |
| 11,017,170 | B2 | 5/2021 | Yin |
| 11,093,547 | B2 | 8/2021 | Su |
| 11,098,303 | B2 | 8/2021 | Zhuang |
| 11,227,219 | B2* | 1/2022 | Roquet ................. G16B 25/00 |
| 11,249,941 | B2 | 2/2022 | Unidad |
| 11,435,905 | B1 | 9/2022 | Kermani |
| 11,755,649 | B2* | 9/2023 | Wei ....................... G06F 16/951 707/722 |
| 11,755,922 | B2* | 9/2023 | Milenkovic ............ G06N 3/123 356/151 |
| 11,763,169 | B2* | 9/2023 | Roquet .................. C40B 50/06 703/11 |
| 2004/0191788 | A1 | 9/2004 | Gleba |
| 2007/0042372 | A1 | 2/2007 | Arita |
| 2010/0199155 | A1 | 8/2010 | Kermani |
| 2011/0172975 | A1 | 7/2011 | Silva Filho |
| 2011/0269119 | A1 | 11/2011 | Hutchison |
| 2017/0109229 | A1 | 4/2017 | Huetter |
| 2017/0134045 | A1 | 5/2017 | Huetter |
| 2018/0046921 | A1 | 2/2018 | Chen |
| 2019/0130280 | A1 | 5/2019 | Erden |
| 2019/0362814 | A1 | 11/2019 | Roquet |
| 2019/0363739 | A1 | 11/2019 | Erlich |
| 2020/0043568 | A1 | 2/2020 | Sikora |
| 2020/0185057 | A1 | 6/2020 | Leake |
| 2020/0193301 | A1 | 6/2020 | Roquet |
| 2021/0024924 | A1 | 1/2021 | Qi |
| 2021/0050073 | A1* | 2/2021 | Chen ...................... G16B 45/00 |
| 2021/0074380 | A1 | 3/2021 | Yekhanin |
| 2021/0079382 | A1 | 3/2021 | Leake |
| 2021/0098081 | A1 | 4/2021 | Yekhanin |
| 2021/0108194 | A1 | 4/2021 | Nathaniel |
| 2021/0166159 | A1 | 6/2021 | Rubenstein |
| 2021/0202032 | A1 | 7/2021 | Krsticevic |
| 2021/0210171 | A1 | 7/2021 | Stirparo |
| 2021/0225461 | A1 | 7/2021 | Merriman |
| 2022/0002781 | A1 | 1/2022 | Harness |
| 2022/0044763 | A1 | 2/2022 | Karimi |
| 2022/0364991 | A1 | 11/2022 | Wanunu |
| 2023/0027270 | A1 | 1/2023 | Rubenstein |
| 2023/0257801 | A1 | 8/2023 | Brodin |
| 2023/0317164 | A1 | 10/2023 | Roquet |
| 2024/0257147 | A1 | 8/2024 | Owen |
| 2025/0020657 | A1 | 1/2025 | Graige |
| 2025/0037039 | A1 | 1/2025 | Rosenstein |

FOREIGN PATENT DOCUMENTS

| | | |
|---|---|---|
| WO | 2018148260 A1 | 8/2018 |
| WO | 2019046768 A1 | 3/2019 |
| WO | 2021072398 A1 | 4/2021 |
| WO | 2021105974 A1 | 6/2021 |
| WO | 2021231493 A1 | 11/2021 |

OTHER PUBLICATIONS

Lu et al., "Design of Nonbinary Error Correction Codes With a Maximum Run-length Constraint to Correct a Single Insertion or Deletion Error for Dna Storage", Institute of Electrical and Electronics Engineers (IEEE), vol. 9, pp. 135354-135363, (2021).

Cai et al., "Correcting a Single Indel/Edit for DNA-Based Data Storage: Linear-Time Encoders and Order-Optimality", EEE Transactions on Information Theory, vol. 67, No. 6, pp. 3438-3451, (2021).

Chen et al., "Multiple Interleaved RS Codes for Data Storage Using Up to Mb-scale Synthetic DNA in Living Cells", Synthetic Biology Journal, vol. 2, Issue 3, pp. 428-443, (2021).

Goto et al., "Coding of Insertion-deletion-substitution Channels Without Markers", 2016 IEEE International Symposium on Information Theory, pp. 635-639, (2016).

Khuat et al., "A Quaternary Code Correcting a Burst of at Most Two Deletion or Insertion Errors in DNA Storage", Entropy, vol. 23, No. 12, p. 1592, (2021).

Kiah et al., "Codes for DNA Sequence Profiles", IEEE Transactions on Information Theory, vol. 62, No. 6, pp. 3125-3146, (2016).

Limbachiya et al., "On Optimal Family of Codes for Archival DNA Storage", Seventh International Workshop on Signal Design and its Applications in Communications, pp. 123-127, (2015).

Yin et al., "Design of Constraint Coding Sets for Archive DNA Storage", IEEE/ACM Transactions on Computational Biology and Bioinformatics, vol. 19, No. 6, pp. 3384-3394, (2022).

Chauhan et al., "Portable and Error-Free DNA-Based Data Storage", 2021 4th International Conference on Recent Developments in Control, pp. 418-421, (2021).

Deng et al., "Optimized Code Design for Constrained DNA Data Storage With Asymmetric Errors", IEEE Access, vol. 7, pp. 84107-84121, (2019).

Jain et al., "Duplication-Correcting Codes for Data Storage in the DNA of Living Organisms", IEEE Transactions on Information Theory, vol. 63, No. 8, pp. 4996-5010 (2017).

Press et al., "Hedges Error-correcting Code for DNA Storage Corrects Indels and Allow Sequence Constraints", Proc Natl Acad Sci USA, vol. 117, No. 31, pp. 18489-18496, (2020).

Wei et al., "Improved Coding Over Sets for DNA-Based Data Storage", IEEE Transactions on Information Theory, vol. 68, No. 1, pp. 118-129, (2022).

Wu et al., "HD-Code: End-to-End High Density Code for DNA Storage", IEEE Transactions on NanoBioscience, vol. 20, No. 4, pp. 455-463, (2021).

Yan et al., "New Levenshtein-Marker Code for DNA-based Data Storage Capable of Correcting Multiple Edit Errors", TechRxiv. (2021).

Hamoum et al., "Channel Model with Memory for DNA Data Storage with Nanopore Sequencing", 2021 11th International Symposium on Topics in Coding , pp. 1-5, (2021).

Dimopoulou et al., "Image storage onto synthetic DNA", Signal Processing: Image Communication, vol. 97, 116331, May 27, 2021, Sections 5.1-5.2; and figure B.3.

Christner et al., "DNA Data Storage—DNA Data Storage Alliance—Rosetta Stone Initiative", Storage Networking Industry Association, Storage Developer Conference, Fremont, CA, Sep. 12-15, 2022.

Gervasio et al., "DNA Data Storage—A Decade of Coding and Decoding, How Far Have We Got?", Storage Networking Industry Association, Storage Developer Conference, Fremont, CA, Sep. 12-15, 2022.

Landsman et al., "DNA Data Storage Alliance: Building a DNA Data Storage Ecosystem", Storage Networking Industry Association, Storage Developer Conference, Fremont, CA, Sep. 12-15, 2022.

Marelli et al., "DNAssim: A Full System Simulator for DNA Storage", Storage Networking Industry Association, Storage Developer Conference, Fremont, CA, Sep. 12-15, 2022.

(56) References Cited

OTHER PUBLICATIONS

Og US et al., "The Looming Need for Molecular Storage", Storage Networking Industry Association, Storage Developer Conference, Fremont, CA, Sep. 12-15, 2022.
Piantanida et al., "Nucleic Acid Memory—Super Resolution Microscopy Enhances Novel Approach to DNA Data Storage", Boise State University, Storage Developer Conference, Fremont, CA, Sep. 12-15, 2022.
Reis et al., "Coding and Decoding, an Experience from a Brazilian Research Center", Storage Networking Industry Association, Storage Developer Conference, Fremont, CA, Sep. 12-15, 2022.
Zhang et al., "Soft-Decision Decoding for DNA-Based Data Storage," 2018 International Symposium on Information Theory and Its Applications (ISITA), Singapore, 2018, pp. 16-20, (Year: 2018).
Zhang et al. Rbec: a Tool for Analysis of Amplicon Sequencing Data from Synthetic Microbial Communities. ISME communications, 1(1), 73. Jan. 17, 2021 (Jan. 17, 2021) whole document (2021).
Qin, et al. "Robust Multi-read Reconstruction from Contaminated Custers Using Deep Neural Network for DNA Storage." arXiv preprint arXiv:2210.11106. Oct. 31, 2022 (Oct. 31, 2022) whole document.
Hamoum et al. "DNA Data Storage Algorithms and Synchronization", Information Theory [math.IT]. University Bretagne Sud, (2022).

* cited by examiner

NESTED ERROR CORRECTION CODES FOR DNA DATA STORAGE

TECHNICAL FIELD

The present disclosure relates to deoxyribonucleic acid (DNA) data storage. In particular, the present disclosure relates to error correction for data stored as a set of synthetic DNA oligos.

BACKGROUND

DNA is a promising technology for information storage. It has potential for ultra-dense 3D storage with high storage capacity and longevity. Currently, technology of DNA synthesis provides tools for synthesis and manipulation of relatively short synthetic DNA chains (oligos). For example, some oligos may include 40 to 350 bases encoding twice that number of bits in configurations that use bit symbols mapped to the four DNA nucleotides or sequences thereof. Due to the relatively short payload capacity of oligos, Reed-Solomon error correction codes have been applied to individual oligos.

There is a need for technology that applies more efficient error correction codes to DNA data storage and retrieval.

BRIEF DESCRIPTION OF THE DRAWINGS

The techniques introduced herein are illustrated by way of example, and not by way of limitation, in the figures of the accompanying drawings in which like reference numerals are used to refer to similar elements.

SUMMARY

Figure 1A:
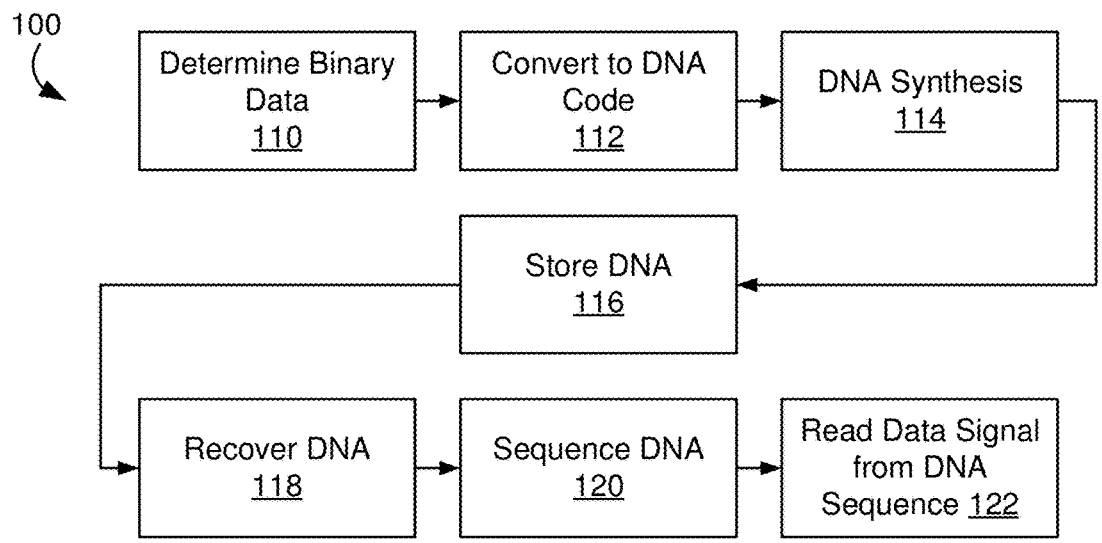
FIG. 1A is a block diagram of a prior art DNA data storage process.

Various aspects for using nested error correction codes for encoding and decoding data stored in an oligo pool for DNA data storage are described.

One general aspect includes a system that includes an encoder configured to: determine a set of oligos for encoding a data unit, where the set of oligos encodes a set of symbols corresponding to the data unit; encode, using a first error correction code for a first codeword size, a first codeword based on a first subset of symbols from the set of symbols; divide the first codeword among a first plurality of oligos; and output write data for the first plurality of oligos for synthesis of the set of oligos.

Implementations may include one or more of the following features. The encoder may be further configured to determine, based on the first error correction code and the first subset of symbols, a first set of redundancy data; and the first plurality of oligos may include the first set of redundancy data. Each oligo in the set of oligos may include an oligo address corresponding to a position of a codeword portion assigned to that oligo relative codeword portions stored in other oligos in the set of oligos. The first plurality of oligos may include a number of oligos corresponding to the first codeword size being greater than 16,000 base pairs. The system may include a decoder configured to: receive read data determined from sequencing the set of oligos; aggregate the read data from the first plurality of oligos corresponding to the first codeword; decode, using the first error correction code and the first codeword, user data from the read data; and output, based on the decoded user data, the data unit. The decoder may be further configured to, prior to decoding the user data using the first codeword: determine insertions and deletions in the first plurality of oligos; correct symbol alignment to compensate for determined insertions and deletions; and identify unreliable data corresponding to the insertions and deletions as erasures for error correction code decoding. The encoder may be further configured to: determine a series of subsets of symbols from the set of symbols, including the first subset of symbols; determine, for each subset of symbols and using the first error correction code, a corresponding first level codeword based on that subset of symbols; aggregate the first level codewords corresponding to the set of symbols; determine, based on a second error correction code having a second codeword size, a second level codeword for the aggregated first level codewords; determine, based on the second error correction code and the aggregated first level codewords, a second level set of redundancy data; divide the first level codewords and the second level set of redundancy data among the set of oligos; and output write data for the set of oligos for the synthesis of the set of oligos. The system may include a decoder configured to: receive read data determined from sequencing the set of oligos; aggregate, for each first level codeword, the read data from a corresponding subset of oligos from the set of oligos; determine, based on the read data, the first level set of redundancy data; attempt to decode, using a first error correction code matrix and the first level set of redundancy data, the first level codewords to decode user data from the read data; aggregate the first level codewords into the second level codeword; determine, based on the read data, the second level set of redundancy data; selectively decode, responsive to a failure to decode at least one first level codeword and using a second error correction code matrix and the second level set of redundancy data, the second level codeword to decode the user data from the read data; and output, based on the decoded user data, the data unit. The second error correction code matrix may be scaled from the first error correction code matrix by replacing each node in the first error correction code matrix with a corresponding scaling matrix. The encoder may be further configured to: determine a number of nested error correction code levels of increasing codeword size; divide the set of symbols for the data unit among a set of oligos; determine first level subsets of the set of symbols corresponding to first level codewords; encode, using the first error correction code, first level codewords and first level redundancy data; allocate the first level redundancy data among the set of oligos; until the number of nested error correction code levels is met, iteratively: aggregate prior level codewords and prior level redundancy data to determine next level sets of symbols; determine, based on the next level sets of symbols and a next level error correction code having a greater codeword size than the prior level codewords, next level codewords and next level redundancy data; and allocate the next level redundancy data among the set of oligos; and output write data for the set of oligos for the synthesis of the set of oligos.

Another general aspect includes a method including: determining a set of oligos for encoding a data unit, where the set of oligos encodes a set of symbols corresponding to the data unit; encode, using a first error correction code for a first codeword size, a first codeword based on a first subset of symbols from the set of symbols; dividing the first codeword among a first plurality of oligos; and outputting write data for the first plurality of oligos for synthesis of the set of oligos.

Implementations may include one or more of the following features. The method may include: determining, based on the first error correction code and the first subset of symbols, a first set of redundancy data; and allocating the first set of redundancy data to the first plurality of oligos. The method may include determining, for each oligo in the set of oligos, an oligo address corresponding to a position of a codeword portion assigned to that oligo relative codeword portions stored in other oligos in the set of oligos. The first plurality of oligos may include a number of oligos corresponding to the first codeword size being greater than 16,000 base pairs. The method may include: receiving read data determined from sequencing the set of oligos; aggregating the read data from the first plurality of oligos corresponding to the first codeword; decoding, using the first error correction code and the first codeword, user data from the read data; and outputting, based on the decoded user data, the data unit. The method may include, prior to decoding the user data using the first codeword: determining insertions and deletions in the first plurality of oligos; correcting symbol alignment to compensate for determined insertions and deletions; and identifying unreliable data corresponding to the insertions and deletions as erasures for error correction code decoding. The method may include: determining a series of subsets of symbols from the set of symbols, including the first subset of symbols; determining, for each subset of symbols and using the first error correction code, a corresponding first level codeword based on that subset of symbols; aggregating the first level codewords corresponding to the set of symbols; encoding, based on a second error correction code having a second codeword size, a second level codeword for the aggregate first level codewords; determining, based on the second error correction code and the aggregate first level codewords, a second level set of redundancy data; dividing the first level codewords and the second level set of redundancy data among the set of oligos; and outputting write data for the set of oligos for the synthesis of the set of oligos. The method may include: receiving read data determined from sequencing the set of oligos; aggregating, for each first level codeword, the read data from a corresponding subset of oligos from the set of oligos; determining, based on the read data, the first level set of redundancy data; attempting to decode, using a first error correction code matrix and the first level set of redundancy data, the first level codewords to decode user data from the read data; aggregating the first level codewords into the second level codeword; determining, based on the read data, the second level set of redundancy data; selectively decoding, responsive to a failure to decode at least one first level codeword and using a second error correction code matrix and the second level set of redundancy data, the second level codeword to decode the user data from the read data; and outputting, based on the decoded user data, the data unit. The method may include determining the second error correction code matrix from the first error correction code matrix by replacing each node in the first error correction code matrix with a corresponding scaling matrix.

Still another general aspect includes a system that includes: means for determining a set of oligos for encoding a data unit, where the set of oligos encodes a set of symbols corresponding to the data unit; means for determining, using a first error correction code for a first codeword size, a first codeword based on a first subset of symbols from the set of symbols; means for dividing the first codeword among a first plurality of oligos; and means for outputting write data for the first plurality of oligos to a synthesis interface for synthesizing the set of oligos.

The present disclosure describes various aspects of innovative technology capable of applying error correction codes to the encoding and decoding of user data stored in a DNA oligo pool. The configuration of nested error correction codes provided by the technology may be applicable to a variety of computer systems used to store or retrieve data stored as a set of oligos in a DNA storage medium. The configuration may be applied to a variety of DNA synthesis and sequencing technologies to generate write data for storage as base pairs and process read data read from those base pairs. The novel technology described herein includes a number of innovative technical features and advantages over prior solutions, including, but not limited to: (1) improved storage efficiency for oligo pools, (2) improved data recovery based on multiple error correction codes for the same user data, and (3) improved decoding efficiency based on selective decoding at different levels of the nested error correction codes.

DETAILED DESCRIPTION

Novel data storage technology is being developed to use synthesized DNA encoded with binary data for long-term data storage. While current approaches may be limited by the time it takes to synthesize and sequence DNA, the speed of those systems is improving and the density and durability of DNA as a data storage medium is compelling. In an example configuration in FIG. 1A, a method 100 may be used to store and recover binary data from synthetic DNA.

At block 110, binary data for storage to the DNA medium may be determined. For example, any conventional computer data source may be targeted for storage in a DNA medium, such as data files, databases, data objects, software code, etc. Due to the high storage density and durability of DNA media, the data targeted for storage may include very large data stores having archival value, such as collections of image, video, scientific data, software, enterprise data, and other archival data.

At block 112, the binary data may be converted to DNA code. For example, a convention computer data object or data file may be encoded according to a DNA symbol index, such as: A or T=1 and C or G=0; A=00, T=01, C-10, and G=11; or a more complex DNA symbol index mapping sequences of DNA bases to predetermined binary data patterns. In some configurations, prior to conversion to DNA code, the source data may be encoded according to an oligo-length format that includes addressing and redundancy data for use in recovering and reconstructing the source data during the retrieval process.

At block 114, DNA may be synthesized to embody the DNA code determined at block 112. For example, the DNA code may be used as a template for generating a plurality of synthetic DNA oligos embodying that DNA code using various DNA synthesis techniques. In some configurations, a large data unit is broken into segments matching a payload capacity of the oligo length being used and each segment is synthesized in a corresponding DNA oligo. In some configurations, solid-phase DNA synthesis may be used to create the desired oligos. For example, each desired oligo may be built on a solid support matrix one base at a time to match the desired DNA sequence, such as using phosphoramidite synthesis chemistry in a four-step chain elongation cycle. In some configurations, column-based or microarray-based oligo synthesizers may be used.

At block 116, the DNA medium may be stored. For example, the resulting set of DNA oligos for the data unit may be placed in a fluid or solid carrier medium. The resulting DNA medium of the set of oligos and their carrier may then be stored for any length of time with a high-level of stability (e.g., DNA that is thousands of years old had been successfully sequenced). In some configurations, the DNA medium may include wells of related DNA oligos suspended in carrier fluid or a set of DNA oligos in a solid matrix that can themselves be stored or attached to another object. A set of DNA oligos stored in a binding medium may be referred to as a DNA storage medium for an oligo pool. The DNA oligos in the pool may relate to one or more binary data units comprised of user data (the data to be stored prior to encoding and addition of syntactic data, such as headers, addresses, synchronization marks, etc.).

At block 118, the DNA oligos may be recovered from the stored medium. For example, the oligos may be separated from the carrier fluid or solid matrix for processing. The resulting set of DNA oligos may be transferred to a new solution for the sequencing process or may be stored in a solution capable of receiving the other polymerase chain reaction (PCR) reagents.

At block 120, the DNA oligos may be sequenced and read into a DNA data signal corresponding to the sequence of bases in the oligo. For example, the set of oligos may be processed through PCR to amplify the number of copies of the oligos from the stored set of oligos. In some configurations, PCR amplification may result in a variable number of copies of each oligo.

At block 122, a data signal may be read from the sequenced DNA oligos. For example, the sequenced oligos may be passed through a nanopore reader to generate an electrical signal corresponding to the sequence of bases. In some configurations, each oligo may be passed through a nanopore and a voltage across the nanopore may generate a differential signal with magnitudes corresponding to the different resistances of the bases. The analog DNA data signal may then be converted back to digital data based on one or more decoding steps, as further described with regard to a method 130 in FIG. 1B.

Figure 1B:
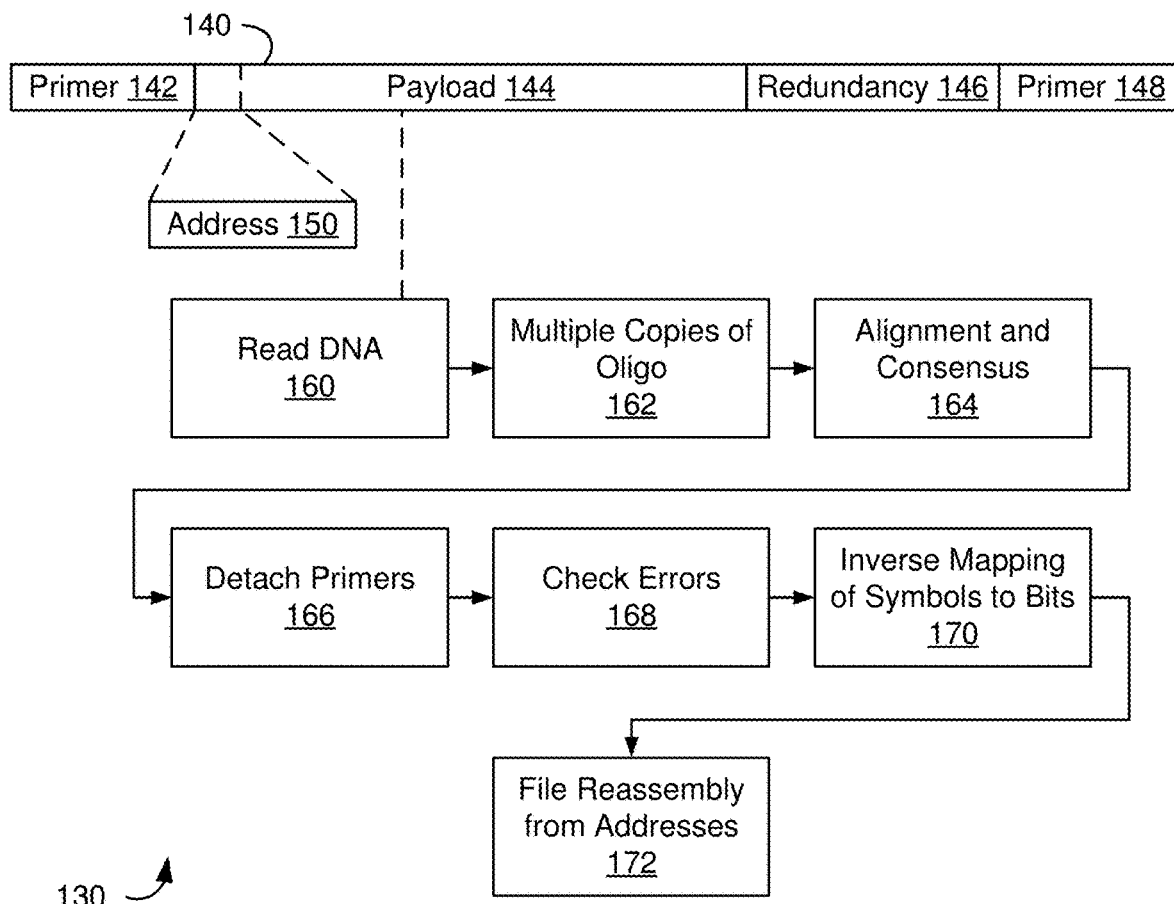
FIG. 1B is a block diagram of a prior art DNA data storage decoding process for oligos encoded with binary data.

In FIG. 1B, method 130 may be used to convert an analog read signal corresponding to a sequence of DNA bases back to the digital data unit that was the original target of the DNA storage process. In the example shown, the original digital data unit, such as a data file, was broken into data subunits corresponding to a payload size of the oligos and the set of oligos corresponding to the subunits of the data unit may be reassembled into the original data unit. An example oligo format 140, including primers 142 and 148 that may be added to support the PCR amplification and sequencing, may include a payload 144 comprising a subunit of the data unit, a redundancy portion 146 for error correction code (ECC) data for that subunit, and an address portion 150 for determining the sequence of the payloads for reassembling the data block. In some configurations, Reed-Solomon error correction codes may be used to determine the redundancy portion 146 for payload 144.

At block 160, DNA base data signals may be read from the sequenced DNA. For example, the analog signal from the nanopore reader may be conditioned (equalized, filtered, etc.) and converted to a digital data signal for each oligo.

At block 162, multiple copies of the oligos may be determined. Through the amplification process, multiple copies of each oligo may be produced and the decoding system may determine groups of the same oligo to process together.

At block 164, each group of the same oligo may be aligned and consensus across the multiple copies may be determined. For example, a group of four copies may be aligned based on their primers and each base position along the set of base values may have a consensus algorithm applied to determine a most likely version of the oligo for further processing, such as, where 3 out of 4 agree, that value is used.

At block 166, the primers may be detached. For example, primers 142 and 148 may be removed from the set of data corresponding to payload data 144, redundancy data 146, and address 150.

At block 168, error checking may be performed on the resulting data set. For example, ECC processing of payload 144 based on redundancy data 146 may allow errors in the resulting consensus data set for the oligo to be corrected. The number of correctable errors may depend on the ECC code used. ECC codes may have difficulty correcting errors created by insertions or deletions (resulting in shifts of all following base values). The size of the oligo payload 144 and portion allocated to redundancy data 146 may determine and limit the correctable errors and efficiency of the data format.

At block 170, the bases or base symbols may be inversely mapped back to the original bit data. For example, the symbol encoding scheme used to generate the DNA code may be reversed to determine corresponding sequences of bit data.

At block 172, a file or similar data unit may be reassembled from the bit data corresponding to the set of oligos. For example, address 150 from each oligo payload may be used to order the decoded bit data and reassemble the original file or other data unit.

Figure 2:
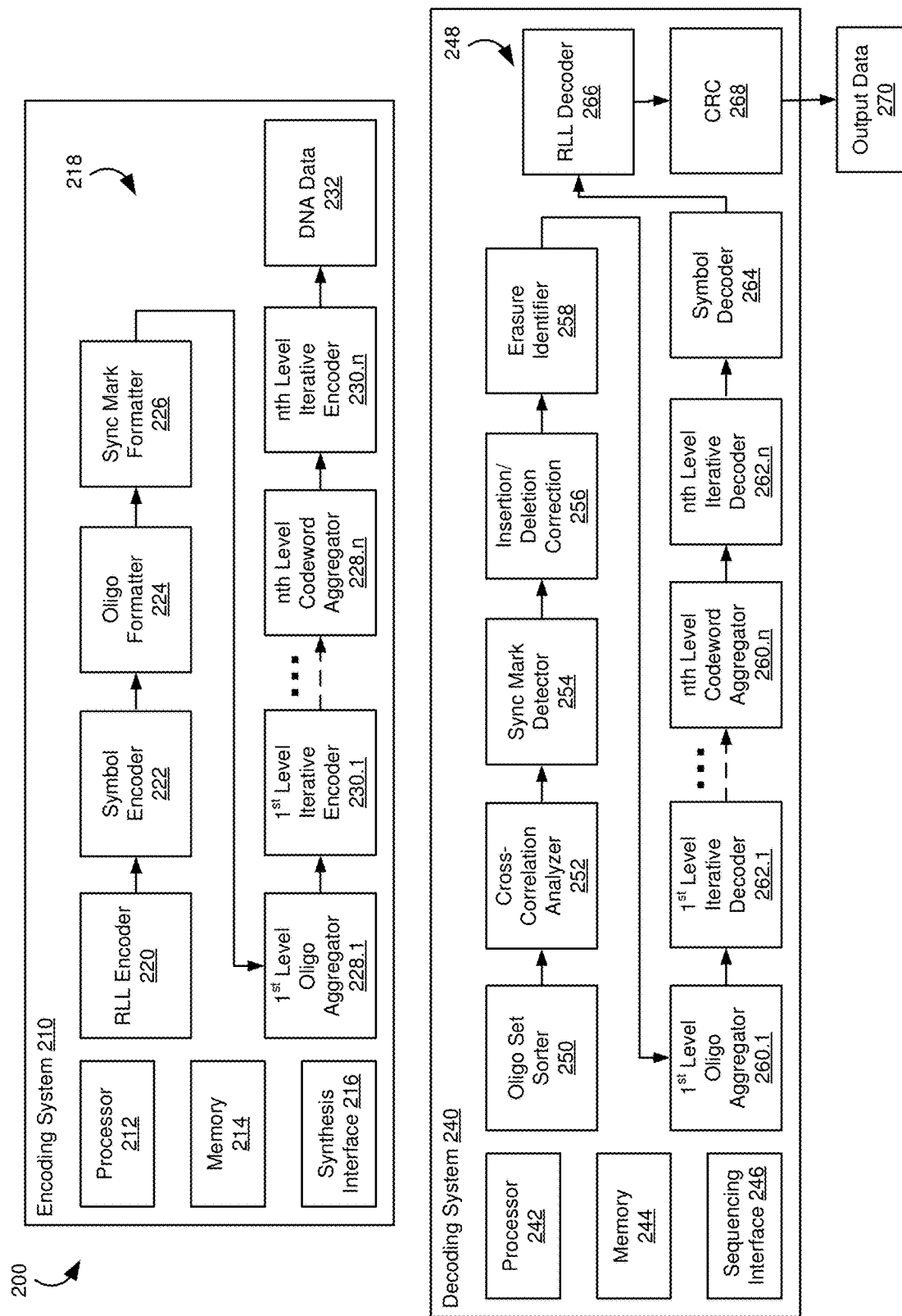
FIG. 2 is a block diagram of an example encoding system and example decoding system for DNA data storage using nested error correction code (ECC) encoders and decoders.

FIG. 2 shows an improved DNA storage system 200 and, more specifically, an improved encoding system 210 and decoding system 240 for using two stage error correction and nested ECC codes to improve data retrieval and efficiency. In some configurations, encoding system 210 may be a first computer system used for determining target binary data, such as a conventional binary data unit, and converting it to a DNA base sequence for synthesis into DNA for storage and decoding system 240 may be a second computer system used for receiving the data signal corresponding to the base sequence read from the DNA.

Encoding system 210 may include a processor 212, a memory 214, and a synthesis system interface 216. For example, encoding system 210 may be a computer system configured to receive or access conventional computer data, such as data stored as binary files, blocks, data objects, databases, etc., and map that data to a sequence of DNA bases for synthesis into DNA storage units, such as a set of DNA oligos. Processor 212 may include any type of conventional processor or microprocessor that interprets and executes instructions. Memory 214 may include a random-access memory (RAM) or another type of dynamic storage device that stores information and instructions for execution by processor 212 and/or a read only memory (ROM) or another type of static storage device that stores static information and instructions for use by processor 212. Encoding system 210 may also include any number of input/output devices and/or interfaces. Input devices may include one or more conventional mechanisms that permit an operator to input information to encoding system 210, such as a keyboard, a mouse, a pen, voice recognition and/or biometric mechanisms, etc. Output devices may include one or more conventional mechanisms that output information to the operator, such as a display, a printer, a speaker, etc. Interfaces may include any transceiver-like mechanism that enables encoding system 210 to communicate with other devices and/or systems. For example, synthesis interface 216 may include a connection to an interface bus (e.g., peripheral component interface express (PCIe) bus) or network for communicating the DNA base sequences for storing the data to a DNA synthesis system. In some configurations, synthesis system interface 216 may include a network connection using internet or similar communication protocols to send a conventional data file listing the DNA base sequences for synthesis, such as the desired sequence of bases for each oligo to be synthesized, to the DNA synthesis system. In some configurations, the DNA base sequence listing may be stored to conventional removable media, such as a universal serial bus (USB) drive or flash memory card, and transferred from encoding system 210 to the DNA synthesis system using the removable media.

In some configurations, a series of processing components 218 may be used to process the target binary data, such as a target data file or other data unit, into the DNA base sequence listing for output to the synthesis system. For example, processing components 218 may be embodied in encoder software and/or hardware encoder circuits. In some configurations, processing components 218 may be embodied in one or more software modules stored in memory 214 for execution by processor 212. Note that the series of processing components 218 are examples and different configurations and ordering of components may be possible without materially changing the operation of processing components 218. For example, in an alternate configuration, additional data processing, such as a data randomizer to whiten the input data sequence, may be used to preprocess the data before encoding. In another configuration, user data from a target data unit may be divided across a set of oligos according to oligo payload size or other data formatting prior to applying any encoding or sync marks may be added after ECC encoding. Other variations are possible.

In some configurations, processing the target data may begin with a run length limited (RLL) encoder 220. RLL encoder 220 may modulate the length of stretches in the input data. RLL encoder 220 may employ a line coding technique that processes arbitrary data with bandwidth limits. Specifically, RLL encoder 220 may bound the length of stretches of repeated bits or specific repeating bit patterns so that the stretches are not too long or too short. By modulating the data, RLL encoder 220 can reduce problematic data sequences that could create additional errors in subsequent encoding and/or DNA synthesis or sequencing. In some configurations, RLL encoder 220 or a similar data modulation component may be configured to modulate the input data to assure that the data pattern used for synchronization marks (added by sync mark formatter 226) does not appear elsewhere in the user data encoded in the oligo.

In some configurations, symbol encoder 222 may include logic for converting binary data into symbols based on the four DNA bases (adenine (A), cytosine (C), guanine (G), and thymine (T)). In some configurations, symbol encoder 222 may encode each bit as a single base pair, such as 1 mapping to A or T and 0 mapping to G or C. In some configurations, symbol encoder 222 may encode two-bit symbols into single bases, such as 11 mapping to A, 00 mapping to T, 01 mapping to G, and 10 mapping to C. More complex symbol mapping can be achieved based on multi-base symbols mapping to correspondingly longer sequences of bit data. For example, a two-base symbol may correspond to 16 states for mapping four-bit symbols or a four-base symbol may map the 256 states of byte symbols. Multi-base pair symbols could be preferable from an oligo synthesis point of view. For example, synthesis could be done not on base pairs but on lager blocks, like 'bytes' correlating to a symbol size, which are prepared and cleaned up earlier (e.g., pre-synthesized) in the synthesis process. This may reduce the amount of synthesis errors. From an encoder/decoder point of view, these physically larger blocks could be treated as symbols or a set of smaller symbols.

In some configurations, oligo formatter 224 may include logic for allocating portions of the target data unit to a set of oligos. For example, oligo formatter 224 may be configured for a predetermined payload size for each oligo and select a series of symbols corresponding to the payload size for each oligo in the set. In some configurations, the payload size may be determined based on an oligo size used by the synthesis system and any portions of the total length of the oligo that are allocated to redundancy data, address data, sync mark data, or other data formatting constraints. For example, for a 150 base pair oligo using two-base symbols may include an eight-base addressing scheme and six four-base sync marks, resulting in 118 base pairs of the target data allocated to each oligo. In some configurations, oligo formatter 224 may insert a unique oligo address for each oligo in the set, such as at the beginning or end of the data payload. The oligo address may allow the encoding and decoding systems to identify the data unit and relative position of the symbols in a particular oligo relative to the other oligos that contribute data to that data unit. For example, decoding system 240 may use position information corresponding to the oligo addresses to reassemble the data unit from a set of oligos in an oligo pool containing one or more data units.

In some configurations, sync mark formatter 226 may include logic for inserting synchronization marks at predetermined intervals among the symbols. For example, sync marks may be inserted every 20 base pairs to divide the data in the oligo into a predetermined number of shorter data segments. In an example configuration, an oligo may have a payload space of 140 base pairs after oligo address space and other (non-sync mark) formatting overhead is allocated, and 5 sync marks of 4 base pairs each may reduce the available capacity for user data to 120 base pairs, resulting in six user data segments of 20 base pairs. Sync marks may be inserted in predetermined positions along the length of the oligo in the payload section and have a predetermined interval of user data symbols or base pairs in between adjacent sync marks. In some configurations, the beginning and end of the oligo payload may be treated as de facto sync marks for determining data segments or a sync mark may be inserted at the beginning and/or end of the user data. Sync marks may be selected to be any sequence of base pairs with good signal-to-noise ratio (SNR) to assist in their detection from sequenced oligos. For example, an alternating sequence of a particular length and frequency may be easier to detect in a background of user data that has been randomized and/or modulated, such as by RLL encoder 220. In some configuration, to avoid false sync mark detection, the selected sync mark pattern may be excluded from user data by a specific modulation code. Sync marks may be used during the decoding process to determine and evaluate user data segments within an oligo to better detect and localize insertions and deletions that are difficult for error correction codes to detect or correct. For example, decoding system 240 may detect synchronization marks and correct symbol alignment prior to attempting iterative decoding with ECC. Use of sync marks is further described below with regard to decoding system 240 and FIGS. 3A-3C.

In some configurations, encoding system 210 may use one or more levels of ECC encoding based on aggregating the data from a number of oligos. For example, encoding system 210 may use low-density parity check (LDPC) codes constructed for larger codewords than can be written to a single oligo. Therefore, data across multiple oligos may be aggregated to form the desired codewords. Similarly, parity or similar redundancy data may not need to be written to each oligo and may instead be written to only a portion of the oligos or written to separate parity oligos that are added to the oligo set for the target data unit. In some configurations, ECC encoding may then be nested for increasingly aggregated sets of oligos, where each level of the nested ECC corresponds to increasingly larger codewords comprised of more oligos. Encoding system 210 may include one or more oligo aggregators 228 and corresponding iterative encoders 230. For example, single level ECC encoding may use first level oligo aggregator 228.1 and first level iterative encoder 230.1 for codewords of 200-400 oligos. A two-level encoding scheme would use first and second level oligo aggregators for and corresponding first and second level iterative encoders, such as for 200 oligo codewords at the first level and 4000 oligo codewords at the second level.

Oligo aggregators 228 may include logic for receiving or selecting the desired number of oligos for encoding a codeword. For example, the ECC configuration may include definition of a codeword size as a multiple of oligos and, at each level, oligo aggregators 228 may determine the requisite number of oligos for the codeword. In the example shown, first level oligo aggregator 228.1 may aggregate a sequential set of 200 oligos for codeword encoding and nth level oligo aggregator 228.n may aggregate a sequential set of 20,000 oligos (100 of the first level codeword sets). The aggregate sets of oligos may be passed to the corresponding iterative encoder 230 for that level.

Iterative encoders 230 can append one or more parity bits to the sets of codeword data for later detection whether certain errors occur during data reading process. For instance, an additional binary bit (a parity bit) may be added to a string of binary bits that are moved together to ensure that the total number of "1"s in the string is even or odd. The parity bits may thus exist in two different types, an even parity in which a parity bit value is set to make the total number of "1"s in the string of bits (including the parity bit) to be an even number, and an odd parity in which a parity bit is set to make the total number of "1"s in the string of bits (including the parity bit) to be an odd number. In some examples, iterative encoders 230 may implement a linear error correcting code, such as LDPC codes or other turbo codes, to generate codewords that may be written to and more reliably recovered from the DNA medium. In some configurations, resulting parity or similar redundancy data may be stored in parity oligos designated to receive the redundancy data for the set of oligos that make up the codeword data. This additional parity data may be encoded using RLL encoder 220, symbol encoder 222, oligo formatter 224, and/or sync mark formatter 226.

The resulting DNA base sequence corresponding to the encoded target data unit may be output from processing components 218 as DNA data 232. For example, the base pair sequences for each oligo in the set of oligos corresponding to the target data unit may be stored as sequence listings for transfer to the synthesis system. In some configurations, the base pair sequences may include the encoded data unit data formatted for each oligo, including address, sync mark, and redundancy data added to the user data for the data unit. The set of oligos may include a plurality of first level codeword sets and their corresponding parity oligos and, in some configurations, nested groups of first level codeword sets, second level codeword sets, and so on for as many levels as the particular recovery configuration supports.

Decoding system 240 may include a processor 242, a memory 244, and a sequencing system interface 246. For example, decoding system 240 may be a computer system configured to receive or access analog and/or digital signal read data from reading sequenced DNA, such as the data signals associated with a set of oligos that have been amplified, sequenced, and read from stored DNA media. Processor 242 may include any type of conventional processor or microprocessor that interprets and executes instructions. Memory 244 may include a random-access memory (RAM) or another type of dynamic storage device that stores information and instructions for execution by processor 242 and/or a read only memory (ROM) or another type of static storage device that stores static information and instructions for use by processor 242. Decoding system 240 may also include any number of input/output devices and/or interfaces. Input devices may include one or more conventional mechanisms that permit an operator to input information to decoding system 240, such as a keyboard, a mouse, a pen, voice recognition and/or biometric mechanisms, etc. Output devices may include one or more conventional mechanisms that output information to the operator, such as a display, a printer, a speaker, etc. Interfaces may include any transceiver-like mechanism that enables decoding system 240 to communicate with other devices and/or systems. For example, sequencing system interface 246 may include a connection to an interface bus (e.g., peripheral component interface express (PCIe) bus) or network for receiving analog or digital representations of the DNA sequences from a DNA sequencing system. In some configurations, sequencing system interface 246 may include a network connection using internet or similar communication protocols to receive a conventional data file listing the DNA base sequences and/or corresponding digital sample values generated by analog-to-digital sampling from the sequencing read signal of the DNA sequencing system. In some configurations, the DNA base sequence listing may be stored to conventional removable media, such as a universal serial bus (USB) drive or flash memory card, and transferred to encoding system 240 from the DNA sequencing system using the removable media.

In some configurations, a series of processing components 248 may be used to process the read data, such as a read data file from a DNA sequencing system, to output a conventional binary data unit, such as a computer file, data block, or data object. For example, processing components 248 may be embodied in decoder software and/or hardware decoder circuits. In some configurations, processing components 248 may be embodied in one or more software modules stored in memory 244 for execution by processor 242. Note that the series of processing components 248 are examples and different configurations and ordering of components may be possible without materially changing the operation of processing components 248. For example, in an alternate configuration, additional data processing for reversing modulation or other processing from encoding system 216 and/or reassembly of decoded oligo data into larger user data units may be included. Other variations are possible.

Decoding system 240 may use a first stage of error correction targeting the elimination of insertion and deletion errors (which create shifts in all following base pairs in a sequence), followed by ECC error correction to address mutation or erasure errors. DNA media and sequencing face three main types of errors: deletion, insertion, and mutation. Mutation errors are most similar to the traditional errors in data storage and may efficiently be handled using ECC correction. Insertion and deletion errors affect the position of all following bits or symbols and may not be effectively handled by ECC. Therefore, preprocessing the oligo sequences for sequence position shifts and, where possible, correcting those position shifts may contribute to more efficient and reliable data reading. The preprocessing stage may reduce the error rate in the oligo sequences significantly prior to applying ECC correction, enabling more efficient ECC codes and more reliable retrieval of data using a first level of ECC encoding in nested ECC configurations. In some configurations, the preprocessing stage may include oligo set sorter 250, cross-correlation analyzer 252, sync mark detector 254, insertion/deletion correction 256, and erasure identifier 258.

In some configurations, oligo set sorter 250 may sort a received group of oligo data sequences into sets of copies. For example, the DNA amplification process may result in multiple copies of some or all oligos and oligo set sorter 250 may sort the oligo data sequences into like sequences. Sorting may be based on tagging during the sequencing process, address data, and/or statistical analysis of sequences (or samples thereof) to determine repeat copies of each oligo. Note that different copies may include different errors and, at this stage, exact matching of all bases in the sequence may not be the sorting criteria. In this regard, each input oligo may generate a set of one or more oligo copies that correspond to the original input oligo data, but may not be identical copies of that data or of one another, depending on when and how the errors were introduced (thus the need for error correction). A set of oligo copies may be processed together, particular through the first stage of processing, to determine or generate a best copy of the oligo for ECC processing.

Figure 3A:
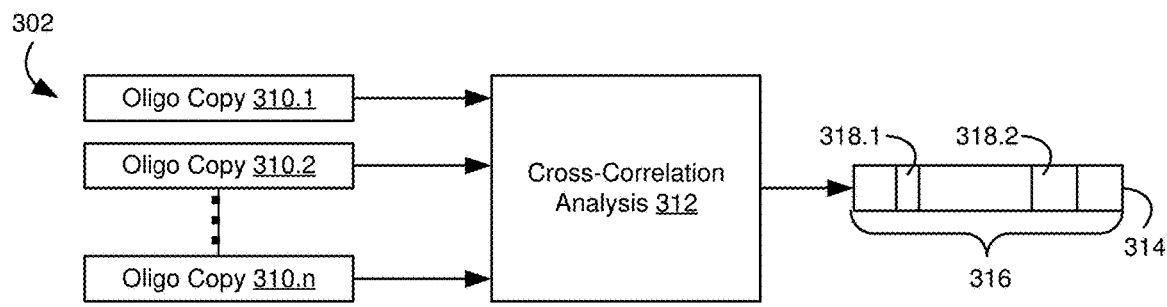
FIGS. 3A, 3B, and 3C are diagrams of oligo processing to correct for insertions and deletions prior to applying ECC processing.

In some configurations, cross-correlation analyzer 252 may include logic for comparing two or more copies of an oligo to determine insertions and deletions. For example, following synthesis and identification of multiple copies of an oligo, insertion and deletion errors would have different locations for different copies and those insertions/deletions could be located by correlation analysis. As shown in FIG. 3A, a cross-correlation analysis 302 may be performed based on any number (greater than 1) of copies of an oligo resulting from multiple syntheses of that oligo from the stored DNA. For example, oligo copies 310.1-310.$n$ may represent a set of oligo copies in the received read data and their corresponding sequencing signals may be provided to cross-correlation analysis 312. Cross-correlation analysis 312 may include functions and logic for identifying the location of insertion and deletion base errors in the input copies to generate a corrected symbol alignment for a "best guess" oligo 314. For example, where correlation analysis identifies an insertion, the specific insertion may be identified and removed to realign the following bases in the oligo. Where correlation analysis identifies a deletion, placeholder values may be added to realign the following bases in the oligo and the positions of the placeholders may be identified as an erasure for correction in the ECC stage. Correction of insertions and deletions in this manner may result in corrected symbol alignment between the read data and the original encoded data to the extent possible. After analysis, uncertain areas where there is insufficient SNR and/or consensus across the copies, segments of bases may be identified and marked as erasures. For example, short shifted regions may have small correlation signals and could be treated as erasures, if SNR is not enough. Resulting oligo 314 may include aligned symbols 316 along the length of the oligo, but with one or more erasure symbols (e.g., erasures 318.1 and 318.2) identified where there were deletions or insufficient SNR or consensus. In some configurations, averaging of correlated segments of bases across multiple copies may provide soft information for use in subsequent ECC processing. For example, the signals from multiple aligned copies may be averaged and statistically processed, providing soft information for each symbol.

Figure 3B:
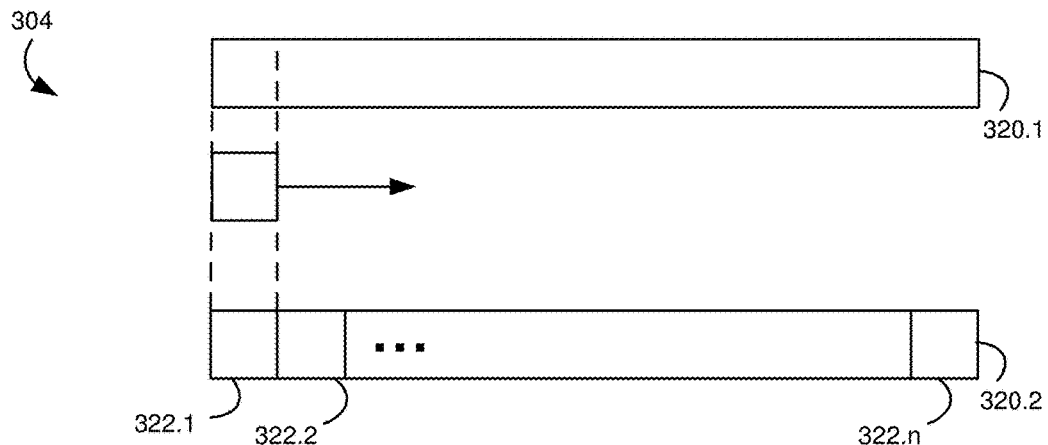

As shown in FIG. 3B, cross-correlation analysis 304 may be conducted using variable length probes (a segment of n bases from one copy of the oligo used for comparison in a sliding window along another copy of the oligo). For example, a first oligo copy 320.1 may be selected as a target for correlation analysis. A second oligo copy 320.2 may be divided into a plurality of probes 322 and probes 322 may be used as reference for correlation analysis of the first copy 320.1 of the oligo. For each probe, a correlation function may be computed between the probe and the first copy 320.1 of the oligo in a sliding window 324 at a plurality of positions along the length of the first copy. The positions of correlation peaks will correspond to position of the probe in the second copy if no insertion or deletion errors are present and both copies of the oligo are the same. In the presence of insertion or deletion errors, the peak positions will be shifted and the size and location of the error may be detected. For example, the delta of the peak toward the start of the oligo may represent a deletion and the delta of the peak toward the end of the oligo may represent and insertion. In some configurations, the probe size n on the reference oligo may be chosen based on the noise in the system. The location from which the probe is selected may be any and multiple probes may be selected along the length of the reference oligo, such as probes 322.1-322.$n$. In some configurations, a probe of size m base pairs may be selected and the location of the probe may start at one end of the reference oligo and be shifted by a step size along the length of the reference oligo to generate multiple probes, such as a series of adjacent probes 322.1-322.$n$ where probe size equals step size. The step size may be as low as one base pair and a step size of one base pair should be able to localize insertion and deletion errors with an accuracy of 1 base pair as long as the SNR is sufficiently high. However, due to the computational requirements to use probes at one base pair steps, larger steps may be selected and somewhat lower accuracy may be an acceptable tradeoff.

While correlation analysis between two base pairs may provide useful information for identifying possible errors, it is not known whether the reference oligo copy or the target oligo copy contains the error. Therefore, correlation analysis across more than two copies enhances the effectiveness of the analysis and the ability to more specifically identify and correct or erasure flag the errors. For example, averaging the results across three or more copies of the same oligo obtained from different syntheses may provide more accurate results, as well as related soft information. Note that cross-correlation analysis can be computationally expensive, particularly as the number of copies increases, and it may be combined with other techniques to localize the analysis to specific regions of an oligo using other techniques. For example, cross-correlation analysis may be combined with the use of sync marks to target the correlation analysis to selected segments where an insertion or deletion is suggested. While cross-correlation an1lyzer 252, sync mark detector 254, insertion/deletion correction 256, and erasure identifier 258 are shown in a linear configuration in FIG. 2, more complex logic for combining sync mark detection and cross-correlation analysis, as well as how those functions drive insertion/deletion correction and identification of erasures is possible.

In some configurations, sync mark detector 254 may include logic to identify periodic sync marks along the length of the oligo to assist in identifying insertion and deletion errors. For example, the sync marks inserted by sync mark formatter 226 may have a defined sync mark spacing or interval corresponding to a number of base pairs that should appear between the sync marks. Sync mark detector 254 may detect the sync marks in the oligo and determine the number of base pairs between the sync marks. The set of base pairs or symbols between sequential sync marks may be referred to as a data segment and have a data segment length that may be compared to the sync mark interval that was used to insert the sync marks. If the number of base pairs between sync marks is greater than the sync mark interval, then an insertion error has occurred. If the number of base pairs between sync marks is less than the sync mark interval, then a deletion error has occurred. Thus, whether an insertion or deletion error occurs in any segment of data between two sync marks may be determined, without impacting the data between other sync marks in the oligo. Data segments with a length equal to the sync mark interval may be presumed not to include an insertion or deletion error and any errors they do contain may be handled by later ECC processing. After insertions and deletions are corrected, such as by insertion/deletion correction 256, the sync marks should align with their original intervals and base pair and symbol alignment within each data segment may be corrected to the extent possible. In some configurations, sync marks may then be removed from the read data prior to ECC processing.

Figure 3C:
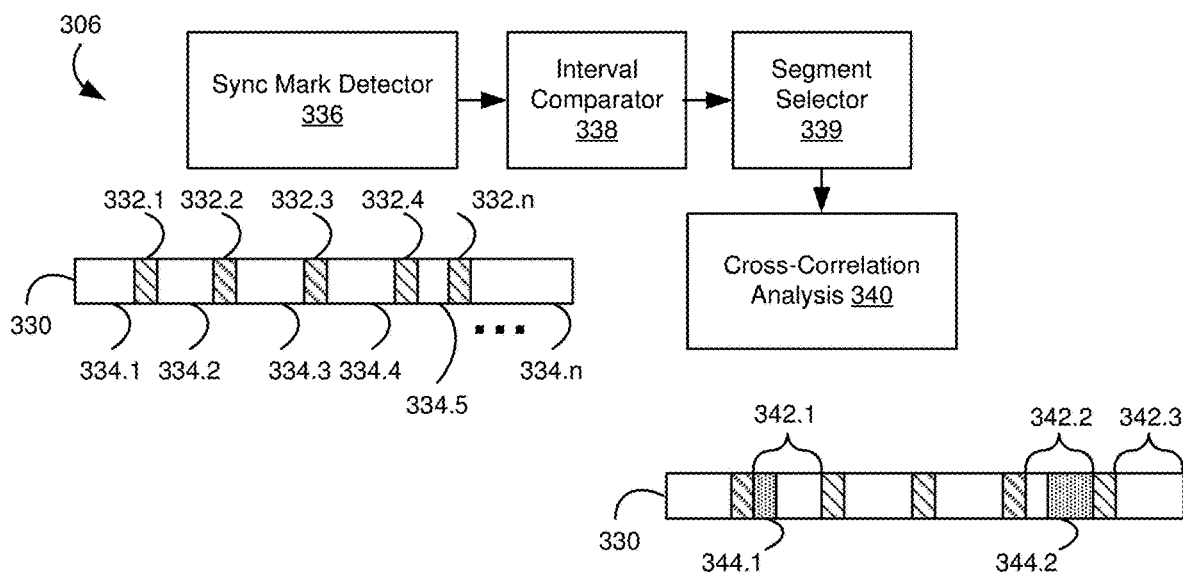

As shown in FIG. 3C, sync mark detection 306 may be followed by selective cross-correlation analysis on data segments to determine insertions and deletions, reducing the amount of cross-correlation analysis that is done. Read data for an oligo 330 is shown. In the example shown, oligo 330 was encoded with a series of five or more sync marks 332.1-332.n defining data segments 334.1-334.n that should have lengths corresponding to a regular sync mark interval. However, insertion and deletion errors may have changed the number of base pairs in some of the segments. For example, segments 334.2 and 334.5 appear shorter (suggesting deletions) and segment 334.n appears longer (suggesting an insertion). Sync mark detector 336 may operate similarly to sync mark detector 254 to detect sync marks 332 based on their sync mark patterns. Interval comparator 338 may determine the length of each data segment and compare it to the predefined sync mark intervals used to encode oligo 330. Interval comparator 338 may determine whether each segment has a length that is greater, less than, or equal to the sync mark interval and identify those data segments that may include insertions or deletions. Following sync mark analysis, no insertion or deletion errors should exist in regions where the sync marks align with the original sync mark interval spacings, such as segments 334.1, 334.3, and 334.4. In some configurations, sync mark detection and analysis may be performed on a single copy of an oligo, such as in cases where multiple copies are not available or cross-correlation analysis is deemed computationally too expensive, which may result in the selected data segments being treated as erasures without any way to localize the insertion or deletion within the data segment. Insertion or deletion within the data region between sync marks may lead to the entire region being identified as an erasure (since, based on sync marks alone, there may be no way to identify where the insertion or deletion occurred in the segment). For example, segment selector 339 may select each data segment that is less or greater than the sync mark interval and pass them to erasure identifier 358 to mark as erasures for ECC processing. Insertion or deletion within a sync mark itself may determine that the segments on both sides of that sync mark are treated as erasures.

As shown in FIG. 3C, the operation of sync mark detector 254, 336 may be combined with the operation of cross-correlation analyzer 252 for selective cross-correlation analysis 340 where multiple copies are available. For example, sync mark detector 336 and interval comparator 338 may be used to identify segments in which insertions and/or deletions exist, and segment selector 339 may selectively pass those segments to cross-correlation analyzer 252 to target those regions for cross-correlation analysis 340 to determine the specific locations of the insertions or deletions and related soft information. This may greatly reduce the amount of cross-correlation analysis to be performed. In the example shown, cross-correlation analysis 340 only needs to selectively process segments 334.2, 334.5, and 334.n. Cross-correlation analysis 340 may localize the deletions in segments 334.2 and 334.5 and enable insertion/deletion correction 256 to insert placeholder values 344.1 to align data segment 342.1 and placeholder values 344.2 to align data segment 342.2 with the original sync mark interval. Cross-correlation analysis 340 may localize the insertions in segment 334.n and enable insertion/deletion correction 256 to remove the inserted base pairs to align data segment 342.3 with the original sync mark interval. Cross-correlation analysis 340 may use a similar approach to that described for FIG. 3B above, based on additional copies of the oligo in the read data and using the sync marks to identify the same corresponding data segment from each copy of the oligo. Probes may be selected within one of the oligo copies and correlation functions may be executed against moving window positions along the target data segment. Because the length of the data segment is substantially smaller than the total oligo, more precise probe sizes and step sizes may be selected for localizing the insertion/deletion event in the data segment.

In some configurations, insertion/deletion correction 256 includes logic for selectively correcting the insertion and deletion errors in an oligo, where possible. For example, insertion/deletion correction 256 may use the output from cross-correlation analyzer 252 and/or sync mark detector 254 to determine correctable insertion/deletion errors. For example, where an insertion or deletion error has occurred between sync marks, the position of subsequent segments may be corrected for the preceding shift in base pair positions to align the symbols in segments without insertions/deletions with their expected positions in the oligo. In some configurations, cross-correlation analysis may enable insertion/deletion correction 256 to specifically identify likely locations of insertion and/or deletion errors at a more granular level, such as symbol, base pair, or other step size. For example, the correlation analysis across more than two copies of an oligo may allow statistical methods and soft information values to be compared to a correction threshold for deleting inserted base pairs and/or inserting padding or placeholder base pairs (which may be identified as erasures by erasure identifier 258) to at least partially correct insertions and/or deletions. The correction threshold may depend on the number of copies being cross-correlated, decoder SNR, size of the insertion/deletion event, a reliability value of the statistical method, and/or the error correction capabilities of the subsequent ECC processing, including the any nested ECC.

In some configurations, erasure identifier 258 may flag segments of base pairs in the oligo as unreliable data erasures in need of ECC error correction. For example, sync mark detector 254 and related analysis may determine one or more segments between sync marks to be identified as erasures for error correction and/or cross-correlation analyzer 252 may determine deletion locations where unknown bases or symbols are missing to be identified as erasures. In some configurations, signal quality, statistical uncertainty, and/or specific thresholds for consensus may cause erasure identifier 258 to identify one or more segments as erasures because the processing by sync mark detector and/or cross-correlation analyzer is inconclusive. For example, erasure identifier 258 may be configured to output an oligo that has had as many base pairs or symbols as possible positively identified as not containing insertion or deletion errors and identify (and localize) as erasures any segments that cannot be determined to be free of insertion or deletion errors prior to performing ECC error correction. Note that mutation errors in DNA storage may be equivalent to the erasure errors ECC are configured to correct and need not be identified in the preprocessing stage. In some configurations, the insertion/deletion corrected output oligo base pair sequence and related erasure tags and/or soft information may be the output of the preprocessing stage of decoding system 240. In some configurations, error rates for oligos may be estimated as ~0.1, including insertion and deletion errors which effectively generate centers of erasure regions after correlation analysis. Actual error rates for oligos may be higher, resulting in a need for error correction codes close to repetition code, which have a code rate of 0.5. This increases the chance of fault decoding by near codewords. Preprocessing to remove insertion and deletion errors, particularly with averaging across multiple copies, may reduce the error rate before ECC processing to enable use of more efficient and reliable ECC codes.

In some configurations, one or more oligo aggregators 260 and iterative decoders 262 may be configured to process the output from the preprocessing stage of decoding system 240. For example, a single "best guess" copy of each unique oligo in a set of oligos for a data unit, including erasure flags and/or soft information, may be passed from preprocessing to ECC decoding. In some configurations, sync marks, address fields, and other formatting data may be removed or ignored by decoding system 240 during ECC processing. Decoding system 240 may use one or more levels of ECC decoding based on aggregating the data from a number of oligos (unique oligos rather than copies of the same oligo). For example, decoding system 240 may use LDPC codes constructed for larger codewords than can be written to or read from a single oligo. Therefore, data across multiple oligos may be aggregated to form the desired codewords. Similarly, parity or similar redundancy data may not be retrieved from each oligo and may instead be read from only a portion of the oligos or from separate parity oligos in the oligo set for the target data unit. In some configurations, ECC decoding may then be nested for increasingly aggregated sets of oligos, where each level of the nested ECC corresponds to increasingly larger codewords comprised of more oligos. Decoding system 240 may include one or more oligo aggregators 260 and corresponding iterative decoders 262. For example, single level ECC encoding may use first level oligo aggregator 260.1 and first level iterative encoder 262.1 for codewords of 200-400 oligos. A two-level encoding scheme would use first and second level oligo aggregators and corresponding first and second level iterative encoders, such as for 200 oligo codewords at the first level and 4000 oligo codewords at the second level.

Figure 4A:
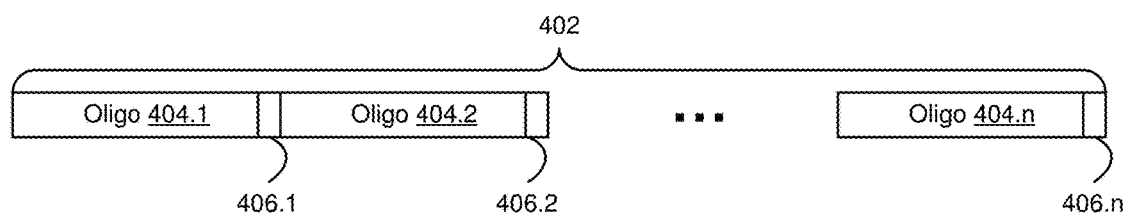
FIGS. 4A and 4B are diagrams of oligo aggregation for applying low-density parity-check (LDPC) encoding/decoding to DNA data storage.

Oligo aggregators 260 may include logic for aggregating the desired number of oligos for decoding a codeword. For example, the ECC configuration may include definition of a codeword size as a multiple of oligos and, at each level, oligo aggregators 260 may determine the requisite number of oligos for the codeword from the preprocessed oligos. As shown in FIG. 4A, a first level codeword 402 of 200-400 oligos may be aggregated by a first level oligo aggregator 260.1. For example, oligos 404 may include a sequence of oligos ordered according to their addresses, such as logical block addresses 406.1-406.$n$. Note that the addresses themselves may not contribute to codeword 402 and may be removed or ignored once the relative positions of the oligo payloads and the corresponding base pairs or symbols are assembled. In the example shown, each oligo may include a payload of 150 base pairs to aggregate a codeword based on 30,000-60,000 base pairs. Approximately 30,000-60,000 base pairs may support 4 KB codewords (32,000 data bits, assuming 1 or 2 base pairs per bit). A 4 KB codeword may be stored in as few as 16,000 base pairs if 2 bit per base pair encoding is used. In another configuration, a ~500 B (~4,000 data bits) codeword using a 2 bit per base pair encoding may be stored in a set of oligos with aggregate payload capacity of 2,000 base pairs, such as ten 200 base pair oligos. In some configurations, a portion of those 200-400 oligos may include parity data for the codeword and, depending on the efficiency of the ECC encoding scheme being used, they may determine a larger number of oligos to support a desired data unit size. For example, a subset of the oligos may be parity oligos encoded with parity data for the codeword. In some configurations, parity oligos may be added to the codeword set of oligoes by appending them to the end of the codeword. For example, oligo 404.$n$ and a number of the preceding oligos may include the parity or other redundancy data for codeword 402.

In some configurations, the sequence data for each oligo may be based on data signals from corresponding pools of amplified oligos and corresponding microfluidics for generating one or more read signals from the one or more copies of that oligo in that pool. In some configurations, each set of the same oligo (from the sample pool 406) may be preprocessed through cross-correlation analyzer 252, sync mark detector 254, insertion/deletion correction 256, and/or erasure identifier 258 to correct for insertions and deletions as described above and oligo aggregators 260 may receive the resulting base sequence data, erasure identifiers, and/or soft information for each oligo. In an example multi-level ECC configuration, first level oligo aggregator 260.1 may aggregate a sequential set of 200 oligos for codeword decoding and nth level oligo aggregator 260.n may aggregate a sequential set of 3,200 oligos (16 of the first level codeword sets). The aggregate sets of oligos may be passed to the corresponding iterative decoder 262 for that level.

In some configurations, iterative decoders 262 may help to ensure that the states at the codeword satisfy the parity constraint by conducting parity error checking to determine whether data has been erased or otherwise lost during data read/write processes. It may check the parity bits appended by iterative encoders 230 during the data encoding process, and compare them with the base pairs or symbols in the oligo sequences aggregated by the corresponding oligo aggregators. Based on the configuration of iterative encoder 230 in the data encoding process, each string of recovered bits may be checked to see if the "1"s total to an even or odd number for the even parity or odd parity, respectively. A parity-based post processor may also be employed to correct a specified number of the most likely error events at the output of the Viterbi-like detectors by exploiting the parity information in the coming sequence. In some configurations, iterative decoders 262 may use soft information received from preprocessing to assist in decode decision-making. When decode decision parameters are met, the codeword may be decoded into a set of decoded base pair and/or symbol values for output or further processing by symbol decoder 264, RLL decoder 266, Cyclic Redundancy Check (CRC) 268, and/or other data postprocessing.

Figure 4B:
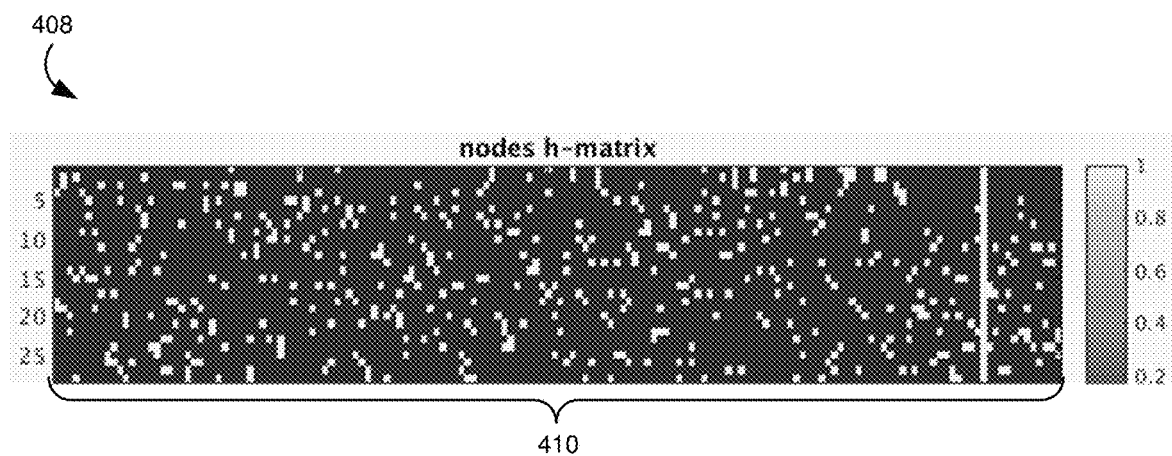

As shown in FIG. 4B, an LDPC code matrix (H-matrix) 408 may be constructed using circulants and/or permutors for decoding an aggregated codeword based on its corresponding parity data and the error correction codes employed. The structure of LDPC H-matrix 408 includes a set of nodes 410, where light squares represent a 1-node and dark squares represent a 0-node. The first level H-matrix 408 may be configured for a first level or primary codeword comparable to a 4 kilobytes (KB) data block. For example, an effective LDPC codeword may typically have a size of 4 KB and higher and aggregating oligos that include 100-200 base pairs of payload data may be used to reach the effective LDPC codeword size. In some configurations, the circulant/permuter size may be equal to the oligo size or oligo payload size to improve erasure recovery efficiency.

Figure 5A:
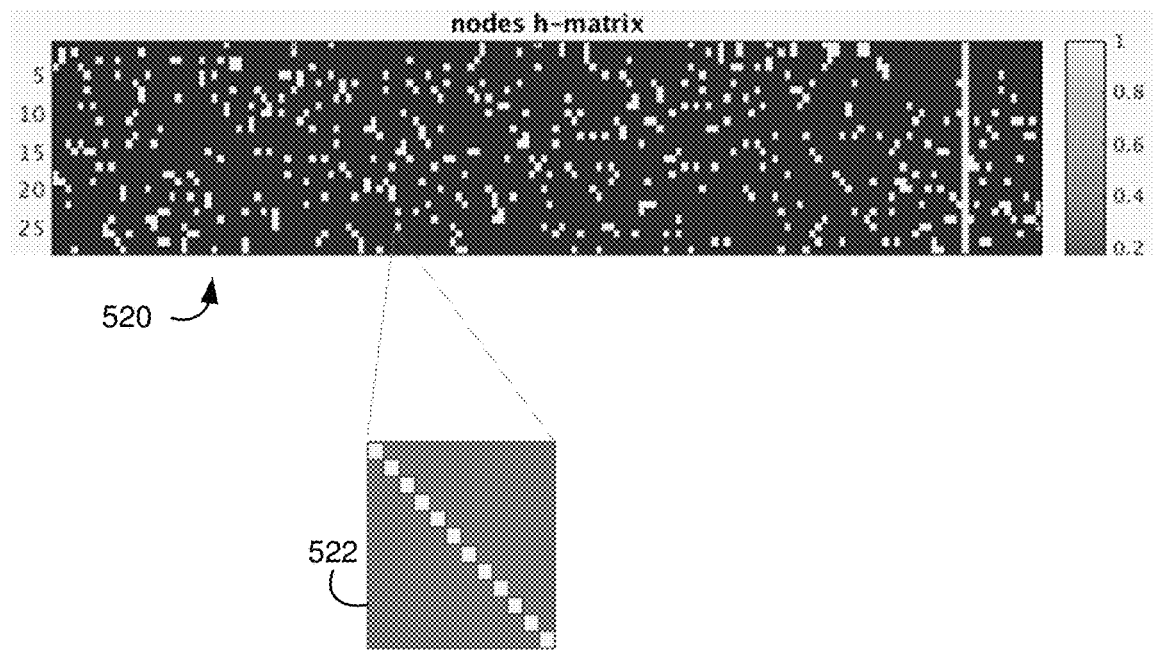
FIGS. 5A and 5B are diagrams of nested aggregation for applying nested ECC encoding/decoding to DNA data storage.

In some configurations, for additional levels of the nested ECC, nodes may be scaled up by n-times to an actual bit/symbol H-matrix of the desired codeword size by replacing each node with an identity matrix of n×n for 1-nodes and a zero matrix of n×n for 0-nodes. The matrices selected for scaling the ECC matrix from a prior level to the next level in the levels of the nested ECC may be referred to as scaling matrices or a scaling matrix. For example, as shown in FIG. 5A, the primary or first level codewords 510.1-510.n may be aggregated into a larger data unit, such as 16 primary codewords for a 64 KB codeword. Corresponding parity data 512 may be determined for the aggregate second level codeword and the second level codeword and parity data may be processed through H-matrix 520 using identify matrix 522 for the nodes, such as a 16×16 identity matrix. In some configurations, scaling may be based on permutation matrices instead of identity matrices. For example, a specific set of permutation matrices may be used for optimal search and elimination of 4-cycles and 6-cycles from the final symbol H-matrix.

Figure 5B:
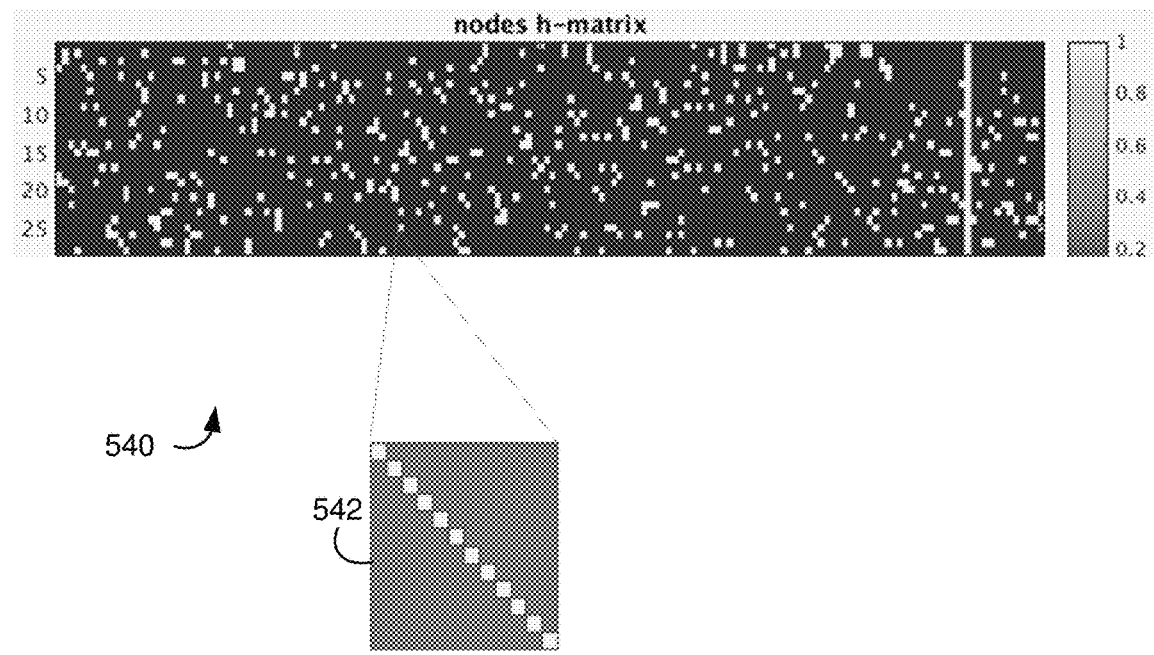

As shown in FIG. 5B, nested ECC levels may be continued for any number of aggregate codewords and corresponding codeword sizes, where codeword sizes increase as the level number increases. For example, the nth level codeword may be an aggregate of n−1 level codeword blocks 530.1-530.n and corresponding parity data 532, where n is the next level codeword and n−1 is the corresponding set of prior level codewords and parity data that support decoding of that next level codeword. Identity matrix 542 may be scaled for whatever the n-value multiple of that aggregate ECC level is. In some configurations, two or more layers may be used and a fractal-like construction may be used. The primary node H-matrix may contain a circulant/permuter in each node. Higher level H-matrix nodes contain identity matrices of the size of the lower layer codeword. H-matrices for higher levels may be simplified to reduce processing demands. In some configurations, the first level codewords (or one or more low-level codewords) may use soft mode LDPC decoding and one or more higher-level codewords may use hard mode LDPC decoding to reduce processing demands.

In some configurations, nested ECC codes based on aggregated layers of codewords may be configured to successfully decode the primary codewords using only the first level iterative decoder 262.1 in most cases. Each higher-level codeword may only be used when a lower level fails to decode all codewords in the group. If some codewords are not decoded at the primary level (or any subsequent level), the next level of code may be very sparse, because most parts of the larger codeword were successfully decoded at the prior level. Higher level code may provide external information to lower level codewords and main decoding may still happen on the lower level, with smaller codewords and smaller resources. Therefore, higher level error correction codes could have a relatively simple construction. In some configurations, LDPC codes at the lower levels could be combined with Reed-Solomon codes on the higher levels.

In some configurations, symbol encoder 264 may be configured to convert the DNA base symbols used to encode the bit data back to their bit data representations. For example, symbol decoder 264 may reverse the symbols generated by symbol encoder 222. In some configurations, symbol decoder 264 may receive the error corrected sequences from iterative decoders 262 and output a digital bit stream or bit data representation. For example, symbol decoder may receive a corrected DNA sequence listing for one or more codewords corresponding to the originally stored data unit and process the corrected DNA sequence listing through the symbol-to-bit conversion to generate a bit data sequence.

In some configurations, RLL decoder 266 may decode the run length limited codes encoded by RLL encoder 220 during the data encoding process. In some configurations, the data may go through additional post-processing or formatting to place the digital data in a conventional binary data format. For example, CRC 268 may provide a simple and reliable way to check if the decoded codeword is correct or it is a near codeword. CRC 268 may be implemented as a division of the codeword on a primitive polynomial in some Galois field. The CRC value may be determined for each binary data unit and added by the originating system or encoding system 210. For example, the remainder of the division may be stored in the codeword information for the later CRC check after decoding. CRC 268 may be particularly advantageous for DNA storage, where error rate is high and near codeword detection is more probable. After a successful CRC check, the output data 270 may then be output to a conventional binary data storage medium, network, or device, such as a host computer, network node, etc. for storage, display, and/or use as a convention binary data file or other data unit.

Figure 6:
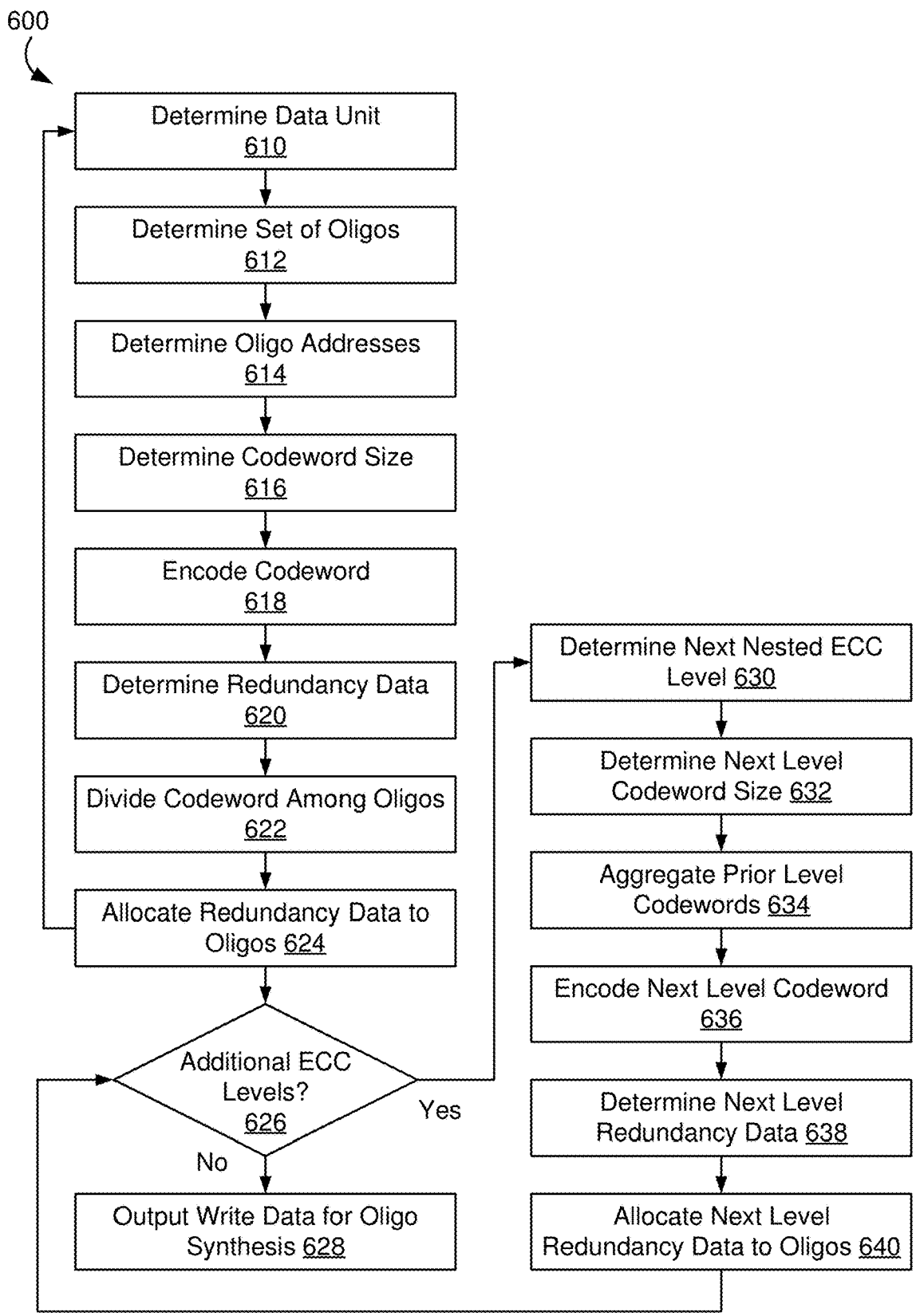
FIG. 6 is an example method for encoding user data in oligos using nested error correction codes, such as using the encoding system of FIG. 2.

As shown in FIG. 6, the encoder in encoding system 210 may be operated according to an example method of encoding user data in oligos using nested error correction codes, i.e., according to the method 600 illustrated by blocks 610-640.

At block 610, a data unit may be determined. For example, the encoder may receive a data unit in a conventional binary data format for storage in a set of oligos.

At block 612, user data for the oligo may be determined. For example, an oligo formatter in the encoder may determine a number of oligos to be used for storing the data unit or a portion thereof.

At block 614, oligo addresses may be determined. For example, the oligo formatter may assign a unique oligo address, such as a logical block address, that allows the encoding and decoding systems to map the contents of that oligo to a position relative to the other oligos for allocating and reassembling the data unit.

At block 616, a codeword size may be determined. For example, the oligo formatter may be configured with a codeword size that is a multiple of the oligo payload size and achieves an efficient data block size for ECC encoding of the data unit (or portions thereof).

At block 618, the codeword may be encoded. For example, the encoder may include an ECC encoder that receives the user data from the data unit as a set of input symbols and applies error correction coding to determine a codeword and redundancy data corresponding to the set of input symbols.

At block 620, redundancy data may be determined. For example, the ECC encoder may generate a set of parity data to be stored with the codeword for use in decoding the codeword with error correction.

At block 622, the codeword may be divided among oligos. For example, the encoder may select a set of oligos with aggregate capacity of at least the codeword size and allocate a subset of the symbols making up the codeword to each oligo.

At block 624, redundancy data may be allocated to oligos. For example, the encoder may distribute the parity data among the oligos including portions of the codeword or may select additional oligos to store the parity data for the codeword. Blocks 610-624 may be repeated for any number of first level codewords to support encoding of one or more data units and their contribution to nested ECC levels and aggregate codewords of increasing size as described below with regard to blocks 626-640.

At block 626, whether additional nested ECC levels are available may be determined. For example, the encoder may be configured for N levels of codewords of increasing size that are comprised of a plurality of lower level codewords. Nested ECC levels may be numbered and processed in sequence until the highest ECC level with the largest codewords has been encoded and allocated to the set of oligos. If no additional levels are indicated, e.g., the prior encoded level was level N, method 600 may proceed to block 628. If the number of nested ECC levels encoded is less than N, method 600 may proceed to block 630.

At block 628, write data may be output for oligo synthesis. For example, the encoder may output write data for the set of oligos including the oligos containing the portions of the first level codewords and parity data, as well as the parity data for each additional nested ECC level calculated.

At block 630, a next nested ECC level may be determined. For example, the encoder may be configured with a series of increasing codeword sizes applied in order from first level codewords (encoded in blocks 610-624) to a largest codeword at level N and the encoder may increment the level by 1 and use the prior nested ECC level codewords to encode a next level codeword.

At block 632, the next level codeword size may be determined. For example, the encoder may be configured with a next codeword size that is a multiple of the prior codeword size, such as 16 prior codewords contributing to a next level codeword.

At block 634, prior level codewords may be aggregated. For example, the encoder may concatenate the data from the prior level codewords as input for encoding the next level codeword.

At block 636, the next level codeword may be encoded. For example, the encoder may include an ECC encoder for the next level of encoding that receives the codewords aggregated at block 634 as a set of input symbols and applies the next level error correction coding to determine a next level codeword and next level redundancy data corresponding to the set of input symbols.

At block 638, next level redundancy data may be determined. For example, the next level ECC encoder may generate a new set of parity data to be stored with the next level codeword for use in decoding that next level codeword with a corresponding error correction matrix.

At block 640, next level redundancy data may be allocated to the oligos. For example, the encoder may distribute the next level parity data among additional oligos to store the parity data for the next level codeword.

Figure 7:
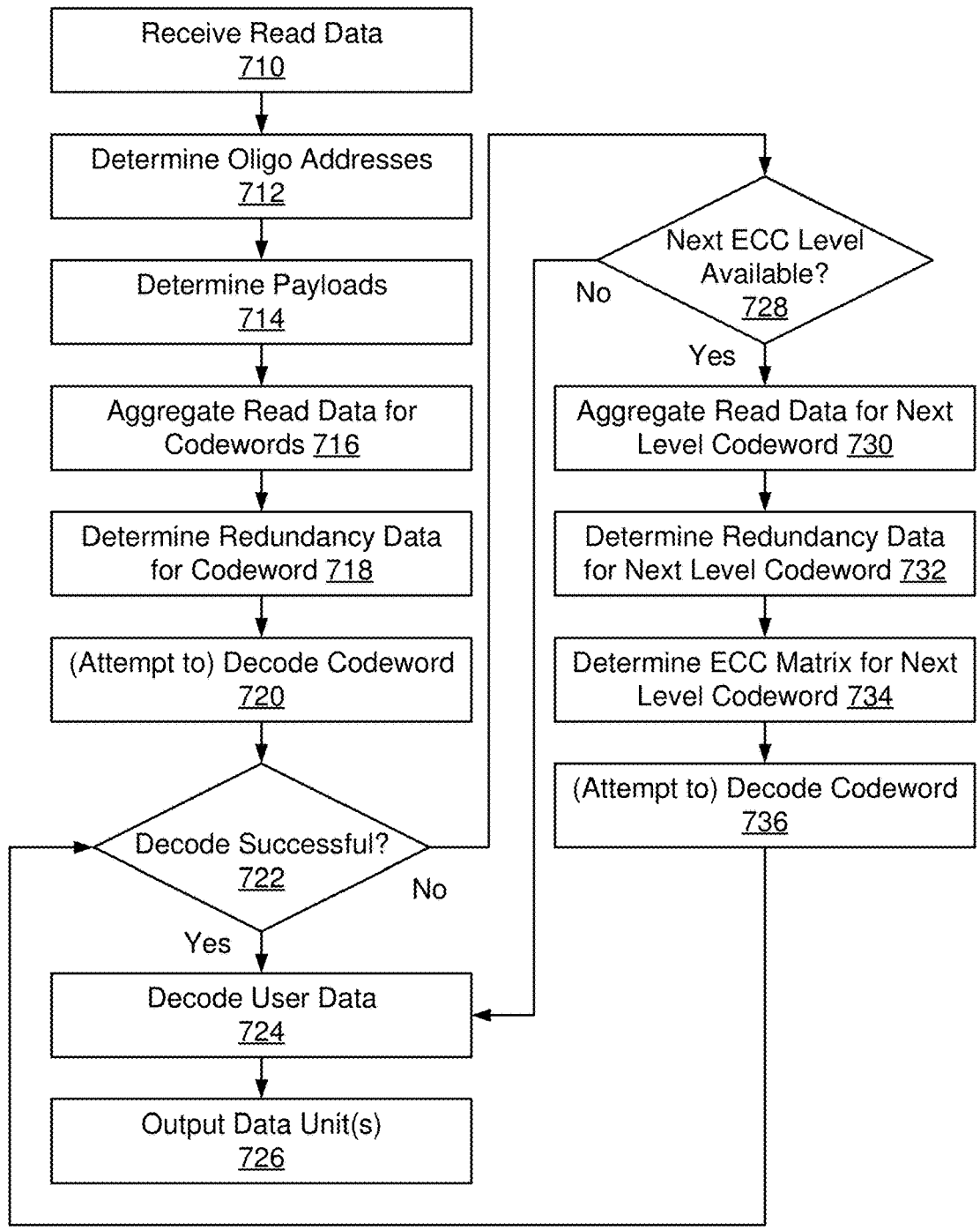
FIG. 7 is an example method for decoding user data using nested error correction codes, such as using the decoding system of FIG. 2.

As shown in FIG. 7, the decoder in decoding system 240 may be operated according to an example method of decoding user data using nested error correction codes, i.e., according to the method 700 illustrated by blocks 710-736.

At block 710, read data may be received. For example, the decoder may receive read data corresponding to a set of oligos for one or more previously encoded data units.

At block 712, oligo addresses may be determined. For example, an oligo set sorter in the decoder may read or receive the oligo addresses associated with the oligo data in the read data to determine the set of oligos and the relative position of the oligo data in a corresponding data unit, as well as identifying the oligos that include redundancy data for various nested levels of error correction.

At block 714, the payloads of the oligos may be determined. For example, the oligo set sorter may extract the read data corresponding to the payload section of each oligo from the read data (e.g., if the read data includes header, footer, or other appended formatting data).

At block 716, read data may be aggregated for codewords. For example, the decoder may include an aggregator for first level codewords to aggregate payload data from sets of oligos (determined by oligo address) that contain portions of the same first level codeword.

At block 718, redundancy data for codewords may be determined. For example, the decoder may determine portions of the payloads or additional oligos that include the parity data for each first level codeword.

At block 720, the codeword may be decoded. For example, the decoder may include a first level ECC decoder and corresponding ECC matrix, such as an LDPC H matrix, that iteratively decodes the aggregated codewords using their corresponding parity data. In some cases, the attempt to decode one or more first level codewords may fail due to erasures exceeding the correction capacity of the ECC configuration used for the first level codewords.

At block 722, whether decode has been successful may be determined. For example, the decoder may evaluate whether all codewords that contribute to a next level codeword successfully decoded. If yes, method 700 may proceed to block 724. If no, method 700 may proceed to block 728.

At block 724, user data may be decoded. For example, the encoder may complete decoding of the user data symbols in the successfully ECC decoded codewords, which may include decoding one or more forms of encoding from encoding system 210, such as symbol decoding, RLL decoding, CRC checks, etc.

At block 726, data units may be output. For example, the decoder may output conventional binary data corresponding to one or more data units assembled from successfully decoded codewords.

At block 728, whether a next nested ECC level is available may be determined. For example, the decoder may be determine whether the configuration supports a next nested ECC level and corresponding aggregate codeword and whether or not the prior level codewords and parity data are available for the next level codeword. If no, method 700 may return to block 724 for application of additional decoding techniques and/or returning the user data with errors. If yes, method 700 may proceed to block 730.

At block 730, read data from prior level codewords may be aggregated for a next level codeword. For example, the decoder may include an aggregator for each level of nested codewords to aggregate payload data from the set of prior level codewords that contain portions of the same next level codeword.

At block 732, redundancy data for the next level codeword may be determined. For example, the decoder may determine additional oligos that include the parity data for each next level codeword.

At block 734, the ECC matrix for the next level codeword may be determined. For example, the encoder may include ECC encoders for each nested ECC level that are configured with an ECC matrix scaled from the prior level ECC matrix based on scaling matrices.

At block 720, the next level codeword may be decoded. For example, the next level ECC decoder and corresponding ECC matrix may iteratively decode the aggregated codewords from the prior level using the corresponding parity data for the next level codeword. In some cases, the attempt to decode one or more next level codewords may fail due to erasures exceeding the correction capacity of the ECC configuration used for the first level codewords and the success of the decode may be evaluated at block 722.

Figure 8:
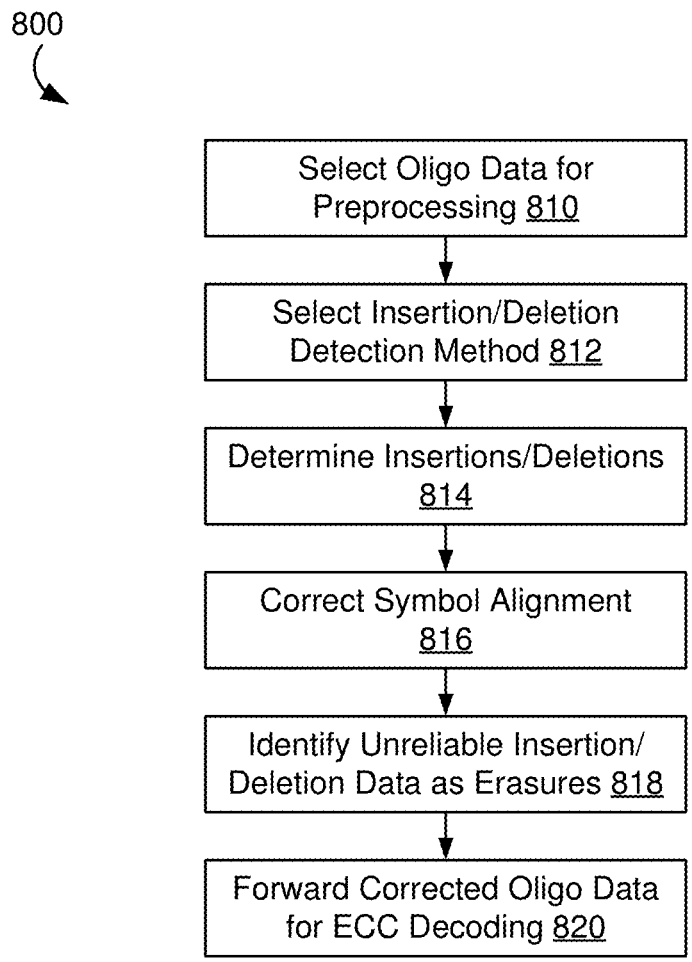
FIG. 8 is an example method for preprocessing to correct for insertions and deletions prior to ECC decoding, such as using the decoding system of FIG. 2.

As shown in FIG. 8, the decoder in decoding system 240 may be operated according to an example method of preprocessing oligo data to correct for insertions and deletions prior to ECC decoding, i.e., according to the method 800 illustrated by blocks 810-820.

At block 810, oligo data may be selected for preprocessing. For example, the decoder may receive read data corresponding to a set of oligos for one or more previously encoded data units and preprocess each oligo (which may include multiple copies of oligo data for that oligo) to correct insertions and deletions for symbol alignment (eliminate position shifts along the length of the oligo).

At block 812, an insertion/deletion detection method may be selected. For example, the decoder may support the use of synchronization marks (if they are present in the encoded data) and/or correlation analysis (if multiple copies of the same oligo are received from sequencing) and may use one or both for detecting and correcting insertions and deletions.

At block 814, insertions and deletions may be determined. For example, the decoder may include a cross-correlation analyzer and sync mark detector that may operate on the oligo data to locate insertions and deletions in the oligo data.

At block 816, symbol alignment may be corrected. For example, the decoder may include insertion/deletion correction logic that uses the insertion and deletion locations determined at block 814 to realign subsequent symbols in the oligo data by removing insertions and/or inserting placeholders for deletions.

At block 818, unreliable insertion/deletion data may be identified as erasures. For example, the decoder may include an erasure identifier configured to tag the locations in the oligo data impacted by the insertions/deletions.

At block 820, the corrected oligo data may be forwarded for ECC decoding. For example, the decoder may pass the insertion/deletion corrected oligo data to ECC decoding, such as method 700.

Technology for improved read channel data detection using ML algorithms is described above. In the above description, for purposes of explanation, numerous specific details were set forth. It will be apparent, however, that the disclosed technologies can be practiced without any given subset of these specific details. In other instances, structures and devices are shown in block diagram form. For example, the disclosed technologies are described in some implementations above with reference to particular hardware.

Reference in the specification to "one embodiment" or "an embodiment" means that a particular feature, structure, or characteristic described in connection with the embodiment is included in at least one embodiment or implementation of the disclosed technologies. The appearances of the phrase "in one embodiment" in various places in the specification are not necessarily all referring to the same embodiment or implementation.

Some portions of the detailed descriptions above may be presented in terms of processes and symbolic representations of operations on data bits within a computer memory. A process can generally be considered a self-consistent sequence of operations leading to a result. The operations may involve physical manipulations of physical quantities. These quantities take the form of electrical or magnetic signals capable of being stored, transferred, combined, compared, and otherwise manipulated. These signals may be referred to as being in the form of bits, values, elements, symbols, characters, terms, numbers, or the like.

These and similar terms can be associated with the appropriate physical quantities and can be considered labels applied to these quantities. Unless specifically stated otherwise as apparent from the prior discussion, it is appreciated that throughout the description, discussions utilizing terms for example "processing" or "computing" or "calculating" or "determining" or "displaying" or the like, may refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosed technologies may also relate to an apparatus for performing the operations herein. This apparatus may be specially constructed for the required purposes, or it may include a general-purpose computer selectively activated or reconfigured by a computer program stored in the computer.

Such a computer program may be stored in a computer readable storage medium, for example, but is not limited to, any type of disk including floppy disks, optical disks, CD-ROMs, and magnetic disks, read-only memories (ROMs), random access memories (RAMs), erasable programmable read-only memories (EPROMs), electrically erasable programmable read-only memories (EEPROMs), magnetic or optical cards, flash memories including USB keys with non-volatile memory or any type of media suitable for storing electronic instructions, each coupled to a computer system bus.

The disclosed technologies can take the form of an entire hardware implementation, an entire software implementation or an implementation containing both hardware and software elements. In some implementations, the technology is implemented in software, which includes but is not limited to firmware, resident software, microcode, etc.

Furthermore, the disclosed technologies can take the form of a computer program product accessible from a non-transitory computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A computing system or data processing system suitable for storing and/or executing program code will include at least one processor (e.g., a hardware processor) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the currently available types of network adapters.

The terms storage media, storage device, and data blocks are used interchangeably throughout the present disclosure to refer to the physical media upon which the data is stored.

Finally, the processes and displays presented herein may not be inherently related to any particular computer or other apparatus. Various general-purpose systems may be used with programs in accordance with the teachings herein, or it may prove convenient to construct more specialized apparatus to perform the required method operations. The required structure for a variety of these systems will appear from the description above. In addition, the disclosed technologies were not described with reference to any particular programming language. It will be appreciated that a variety of programming languages may be used to implement the teachings of the technologies as described herein.

The foregoing description of the implementations of the present techniques and technologies has been presented for the purposes of illustration and description. It is not intended to be exhaustive or to limit the present techniques and technologies to the precise form disclosed. Many modifications and variations are possible in light of the above teaching. It is intended that the scope of the present techniques and technologies be limited not by this detailed description. The present techniques and technologies may be implemented in other specific forms without departing from the spirit or essential characteristics thereof. Likewise, the particular naming and division of the modules, routines, features, attributes, methodologies and other aspects are not mandatory or significant, and the mechanisms that implement the present techniques and technologies or its features may have different names, divisions and/or formats. Furthermore, the modules, routines, features, attributes, methodologies and other aspects of the present technology can be implemented as software, hardware, firmware or any combination of the three. Also, wherever a component, an example of which is a module, is implemented as software, the component can be implemented as a standalone program, as part of a larger program, as a plurality of separate programs, as a statically or dynamically linked library, as a kernel loadable module, as a device driver, and/or in every and any other way known now or in the future in computer programming. Additionally, the present techniques and technologies are in no way limited to implementation in any specific programming language, or for any specific operating system or environment. Accordingly, the disclosure of the present techniques and technologies is intended to be illustrative, but not limiting.

The invention claimed is:

1. A system, comprising:
an encoder circuit configured to:
determine a set of oligos for encoding a data unit, wherein:
the set of oligos encodes a set of symbols corresponding to the data unit; and
each symbol in the set of symbols corresponds to a known sequence of at least one base pair;
encode, using a first error correction code for a first codeword size corresponding to a number of base pairs, a first codeword comprising a first subset of symbols from the set of symbols, wherein the first subset of symbols includes a selected number of base pairs for the first codeword size;
determine, based on the first error correction code and the first subset of symbols, a first set of redundancy data;
divide the first codeword and the first set of redundancy data among a first plurality of oligos from the set of oligos; and
output write data for the first plurality of oligos for synthesis of the set of oligos.

2. The system of claim 1, wherein:
at least one oligo in the set of oligos comprises data from the first set of redundancy data and no symbols from the first codeword.

3. The system of claim 1, wherein each oligo in the set of oligos comprises an oligo address corresponding to a position of a codeword portion assigned to that oligo relative to codeword portions stored in other oligos in the set of oligos.

4. The system of claim 1, wherein the first plurality of oligos includes a number of oligos corresponding to the first codeword size being greater than 16,000 base pairs.

5. The system of claim 1, further comprising:
a decoder circuit configured to:
receive read data determined from sequencing the set of oligos;
aggregate the read data from the first plurality of oligos corresponding to the first codeword;

decode, using the first error correction code and the first codeword, user data from the read data; and
output, based on the decoded user data, the data unit.

6. The system of claim 5, wherein the decoder circuit is further configured to, prior to decoding the user data using the first codeword:
determine insertions and deletions in the first plurality of oligos;
correct symbol alignment to compensate for determined insertions and deletions; and
identify unreliable data corresponding to the insertions and deletions as erasures for error correction code decoding.

7. The system of claim 1, wherein the encoder circuit is further configured to:
determine a series of subsets of symbols from the set of symbols, including the first subset of symbols;
determine, for each subset of symbols and using the first error correction code, a corresponding first-level codeword and first-level set of redundancy data based on that subset of symbols;
aggregate the first-level codewords corresponding to the set of symbols;
determine, based on a second error correction code having a second codeword size, a second-level codeword for the aggregated first-level codewords;
determine, based on the second error correction code and the aggregated first-level codewords, a second-level set of redundancy data;
divide the first-level codewords and the second-level set of redundancy data among the set of oligos; and
output write data for the set of oligos for the synthesis of the set of oligos.

8. The system of claim 7, further comprising:
a decoder circuit configured to:
receive read data determined from sequencing the set of oligos;
aggregate, for each first-level codeword, the read data from a corresponding subset of oligos from the set of oligos;
determine, based on the read data, the first-level set of redundancy data;
attempt to decode, using a first error correction code matrix and the first-level set of redundancy data, the first-level codewords to decode user data from the read data;
aggregate the first-level codewords into the second-level codeword;
determine, based on the read data, the second-level set of redundancy data;
selectively decode, responsive to a failure to decode at least one first-level codeword and using a second error correction code matrix and the second-level set of redundancy data, the second-level codeword to decode the user data from the read data; and
output, based on the decoded user data, the data unit.

9. The system of claim 8, wherein the second error correction code matrix is scaled from the first error correction code matrix by replacing each node in the first error correction code matrix with a corresponding scaling matrix.

10. The system of claim 1, wherein the encoder circuit is further configured to:
determine a number of nested error correction code levels of increasing codeword size, wherein the number of nested error correction code levels is greater than two;
divide the set of symbols for the data unit among the set of oligos;

determine first-level subsets of the set of symbols corresponding to first-level codewords;
encode, using the first error correction code, first-level codewords and first-level redundancy data;
allocate the first-level redundancy data among the set of oligos;
until the number of nested error correction code levels is met, iteratively:
aggregate prior-level codewords and prior-level redundancy data to determine next-level sets of symbols;
determine, based on the next-level sets of symbols and a next-level error correction code having a greater codeword size than the prior-level codewords, next-level codewords and next-level redundancy data; and
allocate the next-level redundancy data among the set of oligos; and
output write data for the set of oligos for the synthesis of the set of oligos.

11. A method comprising:
determining a set of oligos for encoding a data unit, wherein:
the set of oligos encodes a set of symbols corresponding to the data unit; and
each symbol in the set of symbols corresponds to a known sequence of at least one base pair;
encoding, using a first error correction code for a first codeword size corresponding to a number of base pairs, a first codeword comprising a first subset of symbols from the set of symbols, wherein the first subset of symbols includes a selected number of base pairs for the first codeword size;
determining, based on the first error correction code and the first subset of symbols, a first set of redundancy data;
dividing the first codeword among a first plurality of oligos from the set of oligos;
allocating the first set of redundancy data to the first plurality of oligos; and
outputting write data for the first plurality of oligos for synthesis of the set of oligos.

12. The method of claim 11, wherein allocating the first set of redundancy data to the first plurality of oligos comprises allocating at least one oligo that includes data from the first set of redundancy data and no symbols from the first codeword.

13. The method of claim 11, further comprising:
determining, for each oligo in the set of oligos, an oligo address corresponding to a position of a codeword portion assigned to that oligo relative to codeword portions stored in other oligos in the set of oligos.

14. The method of claim 11, wherein the first plurality of oligos includes a number of oligos corresponding to the first codeword size being greater than 16,000 base pairs.

15. The method of claim 11, further comprising:
receiving read data determined from sequencing the set of oligos;
aggregating the read data from the first plurality of oligos corresponding to the first codeword;
decoding, using the first error correction code and the first codeword, user data from the read data; and
outputting, based on the decoded user data, the data unit.

16. The method of claim 15, further comprising, prior to decoding the user data using the first codeword:
determining insertions and deletions in the first plurality of oligos;
correcting symbol alignment to compensate for determined insertions and deletions; and identifying unreliable data corresponding to the insertions and deletions as erasures for error correction code decoding.

17. The method of claim 11, further comprising:
determining a series of subsets of symbols from the set of symbols, including the first subset of symbols;
determining, for each subset of symbols and using the first error correction code, a corresponding first-level codeword and first-level set of redundancy data based on that subset of symbols;
aggregating the first-level codewords corresponding to the set of symbols;
encoding, based on a second error correction code having a second codeword size, a second-level codeword for the aggregate first-level codewords;
determining, based on the second error correction code and the aggregate first-level codewords, a second-level set of redundancy data;
dividing the first-level codewords and the second-level set of redundancy data among the set of oligos; and
outputting write data for the set of oligos for the synthesis of the set of oligos.

18. The method of claim 17, further comprising:
receiving read data determined from sequencing the set of oligos;
aggregating, for each first-level codeword, the read data from a corresponding subset of oligos from the set of oligos;
determining, based on the read data, the first-level set of redundancy data;
attempting to decode, using a first error correction code matrix and the first-level set of redundancy data, the first-level codewords to decode user data from the read data;
aggregating the first-level codewords into the second-level codeword;
determining, based on the read data, the second-level set of redundancy data;
selectively decoding, responsive to a failure to decode at least one first-level codeword and using a second error correction code matrix and the second-level set of redundancy data, the second-level codeword to decode the user data from the read data; and
outputting, based on the decoded user data, the data unit.

19. The method of claim 18, further comprising:
determining the second error correction code matrix from the first error correction code matrix by replacing each node in the first error correction code matrix with a corresponding scaling matrix.

20. A system comprising:
at least one processor;
at least one memory;
means, stored in the at least one processor for execution by the at least one memory, for determining a set of oligos for encoding a data unit, wherein:
  the set of oligos encodes a set of symbols corresponding to the data unit; and
  each symbol in the set of symbols corresponds to a known sequence of at least one base pair;
means, stored in the at least one processor for execution by the at least one memory, for determining, using a first error correction code for a first codeword size corresponding to a number of base pairs, a first codeword based on a first subset of symbols from the set of symbols, wherein the first subset of symbols includes a selected number of base pairs for the first codeword size;
means, stored in the at least one processor for execution by the at least one memory, for determining, based on the first error correction code and the first subset of symbols, a first set of redundancy data;
means, stored in the at least one processor for execution by the at least one memory, for dividing the first codeword and the first set of redundancy data among a first plurality of oligos from the set of oligos; and
means, stored in the at least one processor for execution by the at least one memory, for outputting write data for the first plurality of oligos for synthesis of the set of oligos.

* * * * *